US011421005B2

(12) United States Patent
Lamb, Jr. et al.

(10) Patent No.: US 11,421,005 B2
(45) Date of Patent: Aug. 23, 2022

(54) CHIMERIC CHLOROTOXIN RECEPTORS

(71) Applicant: The UAB Research Foundation, Birmingham, AL (US)

(72) Inventors: Lawrence S. Lamb, Jr., Birmingham, AL (US); Antonio Di Stasi, Birmingham, AL (US); G. Yancey Gillespie, Birmingham, AL (US); Larisa Pereboeva, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 389 days.

(21) Appl. No.: 16/467,467

(22) PCT Filed: Dec. 9, 2017

(86) PCT No.: PCT/US2017/065488
§ 371 (c)(1),
(2) Date: Jun. 6, 2019

(87) PCT Pub. No.: WO2018/107134
PCT Pub. Date: Jun. 14, 2018

(65) Prior Publication Data
US 2020/0055909 A1 Feb. 20, 2020

Related U.S. Application Data

(60) Provisional application No. 62/432,404, filed on Dec. 9, 2016.

(51) Int. Cl.
| | | |
|---|---|---|
| A61K 35/17 | (2015.01) | |
| C07K 14/435 | (2006.01) | |
| A61K 38/17 | (2006.01) | |
| A61K 45/06 | (2006.01) | |
| C07K 14/725 | (2006.01) | |
| C07K 14/705 | (2006.01) | |

(52) U.S. Cl.
CPC ........ *C07K 14/43522* (2013.01); *A61K 35/17* (2013.01); *A61K 38/177* (2013.01); *A61K 38/178* (2013.01); *A61K 38/1767* (2013.01); *A61K 38/1774* (2013.01); *A61K 45/06* (2013.01); *C07K 14/7051* (2013.01); *C07K 14/7056* (2013.01); *C07K 14/70517* (2013.01); *C07K 14/70521* (2013.01); *C07K 14/70578* (2013.01); *C07K 2319/02* (2013.01); *C07K 2319/03* (2013.01); *C07K 2319/30* (2013.01); *C07K 2319/55* (2013.01); *C07K 2319/74* (2013.01)

(58) Field of Classification Search
CPC .... C07K 14/705; C07K 14/725; A61K 35/17; A61K 45/06
See application file for complete search history.

(56) References Cited

U.S. PATENT DOCUMENTS

| | | | |
|---|---|---|---|
| 2011/0091380 A1* | 4/2011 | Jacoby | A61K 47/6415 424/193.1 |
| 2016/0194388 A1 | 7/2016 | Hallahan et al. | |
| 2019/0183930 A1 | 6/2019 | Lamb | |

FOREIGN PATENT DOCUMENTS

| | | | |
|---|---|---|---|
| WO | 2008088422 | 7/2008 | |
| WO | WO-2011053750 A2 * | 5/2011 | ......... A61K 31/4188 |
| WO | 2016166544 A1 | 4/2016 | |
| WO | 2017066481 | 4/2017 | |
| WO | 2018107134 | 6/2018 | |

OTHER PUBLICATIONS

Safdar et al. Targeted nitric oxide delivery preferentially induces glioma cell chemosensitivity via altered p53 and O6-methylguanine-DNA methyltransferase activity. Biotech and BioEng. 110(4): 1211-1220. (Year: 2013).*

Thomas, S., "International Search Report and Written Opinion—International Application No. PCT/US17/65488," dated Apr. 30, 2018.

Priceman, Saul J., et al., "Smart CARs Engineered for Cancer Immunotherapy," Curr Opin Oncol, vol. 27, No. 6, Nov. 2015; pp. 466-474.

Minagawa, Kentaro, et al., "Novel toxicology challenges in the era of chimeric antigen receptor T-cells therapies," Transl Cancer Res., Aug. 16, 2016.

(Continued)

*Primary Examiner* — Karen Cochrane Carlson
(74) *Attorney, Agent, or Firm* — Maynard Cooper & Gale, P. C.; Matthew J. Parker

(57) ABSTRACT

The invention provides chimeric antigen receptor(s) (CAR (s)) that comprise a fusion protein of CTX or any functional variant thereof or a CTX-like peptide or any functional variant thereof as the extracellular antigen recognition moiety of the CAR. CAR(s) comprising CTX, a CTX-like peptide or functional variants of the foregoing are collectively referred to herein as "CTX-CAR(s)." Such CTX-CAR (s) may further comprise additional moieties or domains in the extracellular domain, a transmembrane domain and at least one intracellular! signaling domain. Such CTX-CAR(s) may be expressed in a host cell, such as, but not limited to, an immune effector cell. The present invention also provides methods of treatment (such as, for example, methods for treating cancer) by providing to the patient in need thereof immune effector cells that are engineered to express a CTX-CAR described herein.

17 Claims, 5 Drawing Sheets

Specification includes a Sequence Listing.

(56) References Cited

OTHER PUBLICATIONS

Lamb, Lawrence S., et al., "Engineered Drug Resistant γδ T Cells Kill Glioblastoma Cell Lines during a Chemotherapy Challenge: A Strategy for Combining Chemo-and Immunotherapy," PLOS ONE, vol. 8, Issue 1, Jan. 11, 2013.
Cohen-Inbar, Or, et al., "Glioblastoma multiforme targeted therapy: The Chorotoxin story," Journal of Clinical Neuroscience (2016) http://dx.doi.org/10.1016/j.jocn.2016.04.012.
Niebuhr-Ebel, K., "European Search Report for Europe Application No. 17877604.3" European Patent Office; dated Jun. 17, 2020.
Wang, Yanyao, "Singapore Search Report and Written Opinion for Singapore Application No. 11201904558Y," Intellectual Property Office of Sinagpore; dated Oct. 1, 2020.
Sampson, J.HI., et al., "EGFRv111 mCAR-Modified T-Cell Therapy Cures Mice with Established Intracerebral Glioma and Generates Host Immunity against Tumor-Anitgen Loss," Clinical Cancer Research, vol. 20 No. 4, Feb. 15, 2014; pp. 972-984.
Cheng, Yongjun, et al., "Recent advances in diagnosis and treatment of gliomas using chlorotoxin-based bioconjugates," Am J Nucl Med Mol Imaging, vol. 4, No. 5, Aug. 15, 2014, pp. 385-405.
Wang, Dongrui, et al., "Clorotoxin-directed CAR T cells for specific and effective targeting of glioblastoma," Science Translational Medicine, vol. 12, No. 533, Mar. 4, 2020.

\* cited by examiner

CTX-CAR noCTX-CAR

SEQ ID NO: 1
   Met Cys Met Pro Cys Phe Thr Thr Asp His Gln Met Ala Arg Lys Cys
   Asp Asp Cys Cys Gly Gly Lys Gly Arg Gly Lys Cys Tyr Gly Pro Gln
   Cys Leu Cys Arg
SEQ ID NO: 2
   Ser Gly Gly Gly
SEQ ID NO: 3
   Ser Gly Gly Gly Gly
SEQ ID NO: 4
   ATGTGTATGCCTTGCTTTACGACCGATCATCAGATGGCTAGAAAGTGTGA
   TGACTGTTGTGGAGGCAAGGGACGAGGGAAATGCTATGGACCTCAATGT
   TTGTGTCGC
SEQ ID NO: 5
   Met Arg Leu Asn Leu Ile Lys

CHIMERIC CHLOROTOXIN RECEPTORS

CROSS-REFERENCE TO RELATED APPLICATIONS

This application is a national stage under 35 U.S.C. 371 of International Application No. PCT/US2017/065488, filed Dec. 9, 2017 (currently published). International Application No. PCT/US2017/065488 cites the priority to U.S. Application No. 62/432,404, filed Dec. 9, 2016 (expired).

BACKGROUND OF THE INVENTION

Immunotherapy with antigen-specific T cells has shown promise in the treatment of malignancies in preclinical models as well as in Phase I and II clinical studies. One attractive strategy to generate tumor-specific T cells is by genetic modification with chimeric antigen receptors (CARs), which comprise an extracellular domain comprising an antigen recognition moiety, a transmembrane domain, and at least one intracellular signaling domain (for example an intracellular signaling domain derived from the T-cell receptor CD3-zeta chain often linked to costimulator molecule endodomains).

Chlorotoxins (CTX) belongs to the peptide family of insectotoxins named for their selective paralytic activity on insects and other invertebrates. The primary structure of chlorotoxin comprises 36 amino acids including eight cysteines and is classified as a short-chain, disulfide containing peptide. Research has shown that CTX has tumor binding activity. Studies have shown that CTX was found to bind glioma cells as well as other tumor cells of neuroectodermal origin including melanomas, neuroblastomas, meduloblastomas and small lung carcinomas. However those same studies showed that CTX was unable to bind normal tissues from brain, skin, kidney and lung or other non-tumorigenic tissues derived from neurological diseases such as Parkinson's disease and Alzheimer's disease. Studies have also shown that CTX displays antiangiogenic properties. While the exact target or targets of CTX are not confirmed, it is believed that CTX may act on a specific type of chloride channel found in certain cancer cells, such as glioma cells (CLC-3). Other CTX targets may include matrix metalloproteinase-2 (MMP-2) and Annexin A2. Studies have also shown that CTX has cell penetrating properties and may also be able to enter the brain via the circulatory system although the exact mechanism by which CTX enters the brain has not yet been confirmed.

It would be desirable to leverage the preferential binding of CTX to various types of tumor cells for designing novel CARs comprising CTX and CTX-like peptides (and functional variants of the foregoing) as the antigen recognition moiety.

SUMMARY OF THE INVENTION

The invention provides chimeric antigen receptor(s) (CAR(s)) that comprise a fusion protein of CTX or any functional variant thereof or a CTX-like peptide or any functional variant thereof as the extracellular antigen recognition moiety of the CAR. CAR(s) comprising CTX, a CTX-like peptide or functional variants of the foregoing are collectively referred to herein as "CTX-CAR(s)." Such CTX-CAR(s) may further comprise additional moieties or domains in the extracellular domain, a transmembrane domain and at least one intracellular signaling domain. Such CTX-CAR(s) may be expressed in a host cell, such as, but not limited to, an immune effector cell. In certain embodiments, the immune effector cell is a T cell, a NK cell or a γδ-T cell. The present invention also provides methods of treatment (such as, for example, methods for treating cancer) by providing to the patient in need thereof immune effector cells that are engineered to express a CTX-CAR described herein.

DETAILED DESCRIPTION OF THE INVENTION

Definitions

Figure 1:
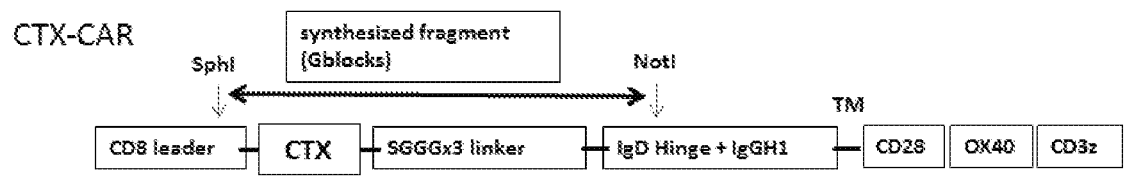
FIG. 1 shows recombinant construct maps showing the design of a preferred CTX-CAR as described in Example 1 (top panel) and the corresponding noCTX-CAR (bottom panel).
Figure 1:
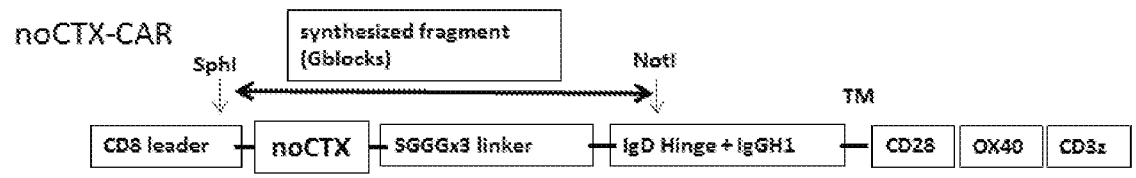
Figure 2:
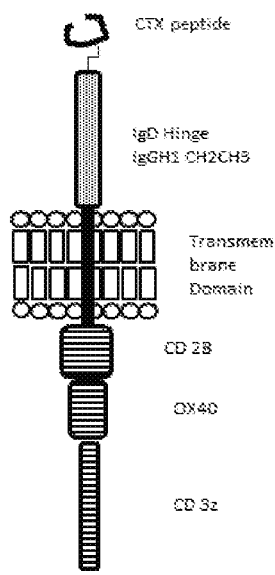
FIG. 2 shows the CTX-CAR and the corresponding noCTX-CAR of FIG. 1 inserted into a membrane.
Figure 2:
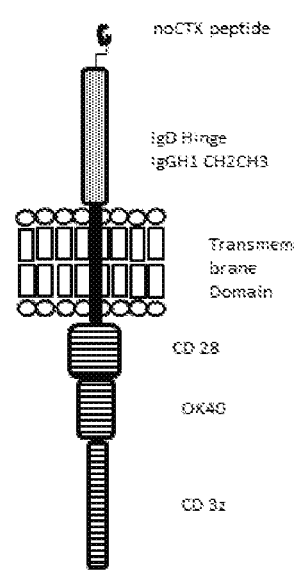
Figure 3:
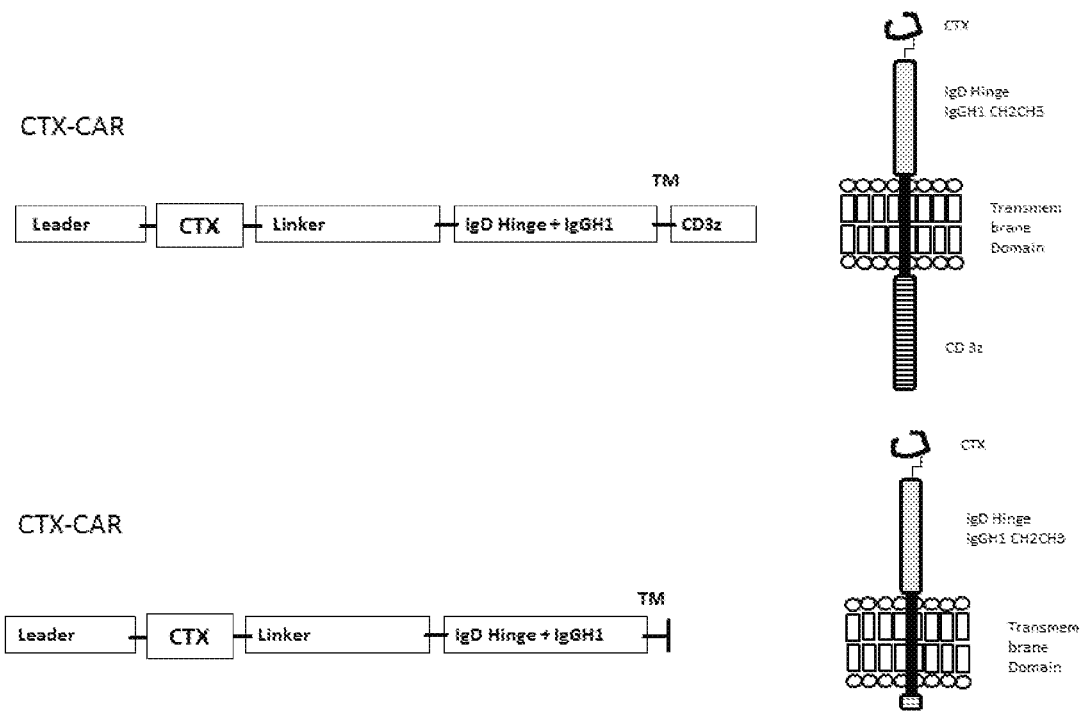
FIG. 3 shows recombinant construct maps showing the design of additional CTX-CARs in accordance with the invention.

As used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

The term "chimeric antigen receptor(s) (CAR(s))," as used herein, refers to artificial T-cell receptors, T-bodies, single-chain immunoreceptors, chimeric T-cell receptors, or chimeric immunoreceptors, for example, and encompass engineered receptors that graft an artificial specificity onto a particular immune effector cell (for example, an antigen recognition domain). CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain that may vary in length and comprises an antigen recognition domain, which may be a tumor associated antigen recognition moiety. In particular aspects, CARs comprise an extracellular domain comprising a CTX polypeptide, a CTX-like polypeptide or functional variants of the foregoing, fused to a transmembrane domain and an intracellular signaling domain/endodomain (in certain embodiments comprising CD3-zeta (CD3ζ). The specificity of other CAR designs may be derived from ligands of receptors (e.g., peptides). In certain cases, the spacing of the antigen-recognition domain can be modified to reduce activation-induced cell death. In certain cases, the intracellular signaling domain of the CARs comprise domains for additional co-stimulatory signaling, such as, but not limited to, FcR, CD27, CD28, CD137, DAP10, and/or OX40 in addition to CD3ζ. In some cases, molecules can be co-expressed with the CAR, including co-stimulatory molecules, reporter genes for imaging (e.g., for positron emission tomography), gene products that allow host cells expressing the CAR to survive in a treatment environment created by an additional therapeutic treatment, gene products that conditionally ablate the host cells expressing the CAR upon addition of a pro-drug, homing receptors, chemokines, chemokine receptors, cytokines, and cytokine receptors.

"Immune effector cell," as that term is used herein, refers to a cell that is involved in an immune response, e.g., in the promotion of an immune effector response. Examples of immune effector cells include T cells, alpha/beta T cells (αβ T-cells) and gamma/delta T cells (γδ T-cells), tumor-infiltrating-lymphocytes (TILs), lymphokine-activated killer (LAK) cells, memory T cells, regulatory T cells, cytotoxic T lymphocytes (CTLs), natural killer T (NKT) cells B cells, natural killer (NK) cells, mast cells, and myeloid-derived phagocytes. Stem cells that differentiate into these cells, can also be used. "Immune effector function" or "immune effector response," as that term is used herein, refers to a function or response, e.g., of an immune effector cell, that enhances or promotes an immune attack of a target cell. For example, an immune effector function or response refers a property of an immune effector cell, such as but not limited to, a T-cell or NK cell, that promotes killing or the inhibition of growth or proliferation, of a target cell. In the case of a T cell, primary stimulation and co-stimulation are non-inclusive examples of immune effector function or response. An immune effector function or response of a naive, stem-cell like, memory, or memory-type T cell includes, but is not limited to, antigen-dependent proliferation.

As used herein, the terms "chlorotoxin" and "CTX" are used interchangeably and refer to a scorpion venom peptide comprising 36 amino acids having the amino acid sequence MCMPCFTDHQ-MARKCDDCCGGKGRGKCYGPQCLCR) (SEQ ID NO: 1) (UniProt Accession #P45639).

As used herein the terms "chlorotoxin-like peptides" or "CTX-like peptides" are used interchangeably herein and refer to other peptides having similar primary structure to CTX and include, but are not limited to, the following peptides:

Bs8 (UniProt #P15229; RCKPCFTTDP QMSKKCADCC GGKGKGKCYG PQCLC); SEQ ID NO: 6;

Insectotoxin-14 (UniProt #P60269; MCMPCFTTDH NMAKKCRDCC GGNGKCFGPQ CLCNR); SEQ ID NO: 7;

Lqh 8/6 (UniProt #P55966; RCSPCFITDQ QMTKKCYDCC GGKGKGKCYG PQCICAPY); SEQ ID NO: 8;

Insectotoxin-13 (UniProt #P60268; MCMPCFTDH QTARRCRDCC GGRGRKCFGQ CLCGYD); SEQ ID NO: 9:

Insectotoxin-I5A (UniProt #P15222; MCMPCFITDP NMAKKCRDCC GGNGKCFGPQ CLCNR); SEQ ID NO: 10;

MeuCITx (UniProt #P86401; TEAMCMPCFT TDHN-MAKKCR DCCGGNGKCF GYQCLCNRG); SEQ ID NO: 11, particularly amino acids 4-38 (resulting from the removal of signal peptide amino acid residues 1-3);

GaTx1 (UniProt #P85066; CGPCFTTDHQ MEQK-CAECCG GIGKCYGPQC LCNR); SEQ ID NO: 12:

Insectotoxin-I5 (UniProt #P60270; MCMPCFTTDP NMANKCRDCC GGGKKCFGPQ CLCNR); SEQ ID NO: 13;

Insectotoxin-II (UniProt #P15220; MCMPCFTTRP DMAQQCRACC KGRGKCFGPQ CLCGYD); SEQ ID NO: 14;

Bm12-b (UniProt #Q9BJW4; MKFLYGIVFI ALFLTVMFAT QTDGCGPCFT TDANMARKCR ECCGGNGKCF GPQCLCNRE); SEQ ID NO: 15, particularly amino acids 25-59 (resulting from the removal of signal peptide amino acid residues 1-24):

BmK CT (UniProt #Q9UADO; MKFLYGIVFI ALFLTVMFAT QTDGCGPCFT TDANMARKCR ECCG-GIGKCF GPQCLCNRI); SEQ ID NO: 16, particularly amino acids 25-59 (resulting from the removal of signal peptide amino acid residues 1-24);

AaCtx (UniProt #P86436; MCIPCFTTNP NMAAKCNACC GSRRGSCRGP QCIC); SEQ ID NO: 17;

MeuCITx-1 (UniProt #P86402; MCMPCFTTRP DMAQQCRDCC GGNGKCFGYQ CLCNR); SEQ ID NO: 18;

Bs14 (UniProt #P59887; CGPCFTKDPE TEKKCATCCG GIGRCFGPQC LCNRGY); SEQ ID NO: 19;

AmmP2 (UniProt #P01498; CGPCFTIDPY TESKCATCCG GRGKCVGPQC LCNRI); SEQ ID NO: 20; and BtlTx3 (UniProt #P81761; MKFLYGVILI ALFLTVMTAT LSEARCGPCF TIDPQTQAKC SECCGRKGGVCKGPQCICGI QY) SEQ ID NO: 21, particularly amino acids 25-61 (resulting from the removal of signal peptide amino acid residues 1-24) and amino acids 25-62 (resulting from the removal of signal peptide amino acid residues 1-24 and pro-peptide amino acid residue 62).

The term "administration" means introducing a compound, biological materials including a cell population (such as a host cells expressing a CTX-CAR of the present disclosure), or a combination thereof, of the present invention into a human or animal subject. One preferred route of administration of the compounds is intravenous. Other preferred routes of administration of the compounds may be intraperitoneal or intrapleural, or via a catheter to the brain. However, any route of administration, such as oral, topical, subcutaneous, peritoneal, intra-arterial, inhalation, vaginal, rectal, nasal, introduction into the cerebrospinal fluid, or instillation into body compartments can be used. Direct injection into a target tissue site such as a solid tumor is also contemplated.

The term "therapeutically effective amount" as used herein refers to that amount of the compound or therapeutically active composition being administered that will relieve to some extent one or more of the symptoms of a disease, a condition, or a disorder being treated. In reference to cancer or pathologies related to unregulated cell division, a therapeutically effective amount refers to that amount which has the effect of (1) reducing the size of a tumor, (2) inhibiting (that is, slowing to some extent, preferably stopping) aberrant cell division, for example cancer cell division, (3) preventing or reducing the metastasis of cancer cells, and/or, (4) relieving to some extent (or, preferably, eliminating) one or more symptoms associated with a pathology related to or caused in part by unregulated or aberrant cellular division, including for example, cancer, and angiogenesis.

The terms "treating" or "treatment" of a disease (or a condition or a disorder) as used herein refer to preventing the disease from occurring in a human subject or an animal subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and/or causing regression of the disease. With regard to cancer, these terms also mean that the life expectancy of an individual affected with a cancer may be increased or that one or more of the symptoms of the disease will be reduced. With regard to cancer, "treating" also includes reducing a cancer, enhancing or prolonging an anti-tumor response in a subject.

As used herein any form of administration of a "combination", "combined therapy" and/or "combined treatment regimen" refers to at least two therapeutically active drugs or compositions which may be administered simultaneously, in either separate or combined formulations, or sequentially at different times separated by minutes, hours or days, but in some way act together to provide the desired therapeutic response.

The term "enhancing", as used herein, refers to allowing a subject or tumor cell to improve its ability to respond to a treatment disclosed herein. For example, an enhanced response may comprise an increase in responsiveness of at least 5&% 10%, 15%, 20%, 25&% 30%, 35%, 40%, 45%, 50%, 55%, 60%, 65%, 70%, 75%, 80%, 85%, 90%, 95% or 98% or more. As used herein, "enhancing" can also refer to enhancing the number of subjects who respond to a treatment, such as a combination therapy comprising a CTX-CAR of the present disclosure and chemotherapy, drug-resistant immunocompetent cells, and immune checkpoint inhibitors. For example, an enhanced response may refer to a total percentage of subjects who respond to a treatment wherein the percentage is of at least 5%, 10%, 15%, 20%, 25%, 30%, 35%, 40%, 45%, 50%, 55%, 60&% 65%, 70%, 75%, 80%, 85%, 90%, 95% or 98% or more.

The terms "subject" and "patient" as used herein include humans, mammals (e.g., cats, dogs, horses, etc.), living cells, and other living organisms. A living organism can be as simple as, for example, a single eukaryotic cell or as complex as a mammal. Typical patients are mammals, particularly primates, especially humans. For veterinary applications, a wide variety of subjects will be suitable, e.g., livestock such as cattle, sheep, goats, cows, swine, and the like, poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Preferably, a system includes a sample and a subject. The term "living host" refers to host or organisms noted above that are alive and are not dead. The term "living host" refers to the entire host or organism and not just a part excised (e.g., a liver or other organ) from the living host.

The terms "gamma delta T-cells", "γδ T-cells" or "γδT" as used interchangeably herein refers to a small subset of T-cells that express a distinct T-cell receptor (TCR) on their surface. A majority of T-cells have a TCR composed of two glycoprotein chains called α- and β-TCR chains. In contrast, in γδ T-cells, the TCR is made up of one γ-chain and one δ-chain. This group of T-cells is usually much less common than αβ T-cells, but are found at their highest abundance in the gut mucosa, within a population of lymphocytes known as intraepithelial lymphocytes (IELs). The antigenic molecules that activate γδ T-cells are still largely unknown. However, γδ T-cells are peculiar in that they do not seem to require antigen processing and MHC presentation of peptide epitopes although some recognize MHC class IB molecules. Furthermore, γδ T-cells are believed to have a prominent role in recognition of lipid antigens, and to respond to stress-related antigens such as, MIC-A and MIC-B.

The term "antibody," as used herein, refers to an immunoglobulin or a part thereof, and encompasses any polypeptide comprising an antigen-binding site regardless of the source, species of origin, method of production, and characteristics. Antibodies may be comprised of heavy and/or light chains or fragments thereof. Antibodies or antigen-binding fragments, variants, or derivatives thereof of the invention include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies. ScFv molecules are known in the art and are described, e.g., in U.S. Pat. No. 5,892,019. Antibody molecules of the invention can be of any type (e.g., IgG, IgE, IgM, IgD, IgA, and IgY), class (e.g., IgG1, IgG2, IgG3. IgG4, IgA1 and IgA2) or subclass of immunoglobulin molecule.

The term "biologic therapeutic" or "biopharmaceutical", as used herein, refers to any medicinal product manufactured in or extracted from biological sources. Biopharmaceuticals are distinct from chemically synthesized pharmaceutical products. Examples of biopharmaceuticals include vaccines, blood or blood components, allergenics, somatic cells, gene therapies, tissues, recombinant therapeutic proteins, including antibody therapeutics and fusion proteins, and living cells. Biologics can be composed of sugars, proteins or nucleic acids or complex combinations of these substances, or may be living entities such as cells and tissues. Biologics are isolated from a variety of natural sources-human, animal or microorganism—and may be produced by biotechnology methods and other technologies. Specific examples of biologic therapeutics include, but are not limited to, immunostimulatory agents, T cell growth factors, interleukins, antibodies, fusion proteins and vaccines, such as cancer vaccines.

The term "cancer", as used herein, shall be given its ordinary meaning, as a general term for diseases in which abnormal cells divide without control. In particular, and in the context of the embodiments of the present invention, cancer refers to angiogenesis-related cancer, such as, but not limited to, glioma. Cancer cells can invade nearby tissues and can spread through the bloodstream and lymphatic system to other parts of the body. There are many types of cancer. Carcinoma is cancer that begins in the skin or in tissues that line or cover internal organs. Glioma is a tumor that arises from the supportive ("gluey") tissue of the brain, called glia, which helps to keep the neurons in place and functioning well. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, gliomas, carcinomas, and lymphomas. Leukemias (cancers of the blood) generally do not form solid tumors.

Representative cancers include, but are not limited to, Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma. Childhood Cerebellar; Astrocytoma, Childhood Cerebral; Bile Duct Cancer. Extrahepatic; Bladder Cancer; Bladder Cancer, Childhood; Bone Cancer, Osteosarcoma/Malignant Fibrous Histiocytoma; Glioblastoma, Childhood; Glioblastoma, Adult; Brain Stem Glioma. Childhood; Brain Tumor. Adult; Brain Tumor, Brain Stem Glioma, Childhood; Brain Tumor. Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/ Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer. Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia. Acute Myeloid. Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's. Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma. Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia Chronic; Myeloid Leukemia Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Neurofibroma; Non-Hodgkin's Lymphoma, Adult; Non-Hodgkin's Lymphoma. Childhood. Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood', Pancreatic Cancer. Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma. Childhood; Salivary Gland Cancer; Salivary Gland' Cancer, Childhood; Sarcoma, Ewing's Family of Tumors; Sarcoma, Kaposi's; Sarcoma (Osteosarcoma)/Malignant Fibrous Histiocytoma of Bone; Sarcoma. Rhabdomyosarcoma, Childhood; Sarcoma. Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary. Metastatic; Stomach (Gastric) Cancer; Stomach (Gastric) Cancer, Childhood; Supratentorial Primitive Neuroectodermal Tumors, Childhood; T-Cell Lymphoma. Cutaneous; Testicular Cancer; Thymoma. Childhood; Thymoma. Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor, among others.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult. Benign tumors have less of a tendency to invade and are less likely to metastasize.

The term "fusion protein", as used herein, refers to chimeric molecules, which comprise, for example, an antigen recognition domain for example, CTX, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The terms "reducing a cancer," "inhibition of cancer," "inhibiting cancer" and similar terms are used interchangeably herein and refer to one or more of a reduction in the size or volume of a tumor mass, a decrease in the number of metastasized tumors in a subject, a decrease in the proliferative status (the degree to which the cancer cells are multiplying) of the cancer cells, and the like.

The term "expressed" or "expression" as used herein refers to the transcription from a DNA sequence to give an RNA molecule at least complementary in part to a region of one of the two nucleic acid strands of the DNA sequence. The term "expressed" or "expression" as used herein also refers to the translation from said RNA molecule to give a protein, a polypeptide, or a portion or fragment thereof.

The term "promoter" as used herein refers to the DNA sequence that determines the site of transcription initiation from an RNA polymerase. A "promoter-proximal element" may be a regulatory sequence within about 200 base pairs of the transcription start site.

The term "recombinant cell" refers to a cell that has a new combination of nucleic acid segments that are not normally present in the cell in nature and/or not covalently linked to each other in nature. A new combination of nucleic acid segments can be introduced into an organism using a wide array of nucleic acid manipulation techniques available to those skilled in the art. A recombinant cell can be a single eukaryotic cell, or a single prokaryotic cell, or a mammalian cell. The recombinant cell may harbor a vector that is extragenomic. An extragenomic nucleic acid vector does not insert into the cell's genome. A recombinant cell may further harbor a vector or a portion thereof that is intragenomic. The term "intragenomic" defines a nucleic acid construct incorporated within the recombinant cell's genome.

The terms "recombinant nucleic acid" and "recombinant DNA" as used herein refer to combinations of at least two nucleic acid sequences that are not naturally found in a eukaryotic or prokaryotic cell and/or not covalently linked to each other naturally in a eukaryotic or prokaryotic cell. The recombinant nucleic acid sequences include, but are not limited to, one or more of a nucleic acid to be expressed in a host cell, nucleic acid vectors, gene expression regulatory elements, origins of replication, suitable gene sequences that when expressed confer antibiotic resistance, protein-encoding sequences, and the like. The term "recombinant polypeptide" is meant to include a polypeptide produced by recombinant DNA techniques (such as using a recombinant nucleic acid) such that it is distinct from a naturally occurring polypeptide either in its location, concentration, purity or structure. Generally, such a recombinant polypeptide will be present in a cell in an amount different from that normally observed in nature.

The terms "operably" or "operatively linked" as used herein refer to the configuration of the coding and control sequences so as to perform the desired function. Thus, control sequences operably linked to a coding sequence are capable of effecting the expression of the coding sequence. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "heterologous" and "exogenous" as they relate to nucleic acid sequences such as coding sequences and control sequences denote sequences that are not normally associated with a region of a recombinant construct or with a particular chromosomal locus, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct, which is not normally present in the host cell, would be considered heterologous for purposes of this invention Preferably, the promoter will be modified by the addition or deletion of sequences, or replaced with alternative sequences, including natural and synthetic sequences as well as sequences that may be a combination of synthetic and natural sequences. Many eukaryotic promoters contain two types of recognition sequences: the TATA box and the upstream promoter elements. The former, located upstream of the transcription initiation site, is involved in directing RNA polymerase to initiate transcription at the correct site, while the latter appears to determine the rate of transcription and is upstream of the TATA box. Enhancer elements can also stimulate transcription from linked promoters, but many function exclusively in a particular cell type. Many enhancer/promoter elements derived from viruses, e.g., the SV40, the Rous sarcoma virus (RSV), and CMV promoters are active in a wide array of cell types, and are termed "constitutive" or "ubiquitous." The nucleic acid sequence inserted in the cloning site may have any open reading frame encoding a polypeptide of interest, with the proviso that where the coding sequence encodes a polypeptide of interest, it should lack cryptic splice sites that can block production of appropriate mRNA molecules and/or produce aberrantly spliced or abnormal mRNA molecules.

The termination region that is employed primarily will be one of convenience, since termination regions appear to be relatively interchangeable. The termination region may be native to the intended nucleic acid sequence of interest, or may be derived from another source.

The term "vector" as used herein refers to a polynucleotide comprised of single strand, double strand, circular, or supercoiled DNA or RNA. A typical vector may be comprised of the following elements operatively linked at appropriate distances for allowing functional gene expression: replication origin, promoter, enhancer, 5' mRNA leader sequence, ribosomal binding site, nucleic acid cassette, termination and polyadenylation sites, and selectable marker sequences. One or more of these elements may be omitted in specific applications. The vector may also contain a nucleic acid cassette, which can include a restriction site for insertion of the nucleic acid sequence to be expressed. In a functional vector the nucleic acid cassette contains the nucleic acid sequence to be expressed including translation initiation and termination sites.

A vector is constructed so that the particular coding sequence (for example, a coding sequence for a CTX-CAR of the present disclosure) is located in the vector with the appropriate control sequences, the positioning and orientation of the coding sequence with respect to the control sequences being such that the coding sequence is operably linked and/or is transcribed "under the control" of the control sequences. Modification of the sequences encoding the particular protein of interest may be desirable to achieve this end. For example, in some cases it may be necessary to modify the sequence so that it may be operably linked to the control sequences with the appropriate orientation or to maintain the reading frame. The control sequences and/or other regulatory sequences may be ligated to the coding sequence prior to insertion into a vector. Alternatively, the coding sequence can be cloned directly into an expression vector that already contains the control sequences and an appropriate restriction site that is in reading frame with and under regulatory control of the control sequences.

The terms "transformation", "transduction" and "transfection" all denote the introduction of a polynucleotide into a recipient cell or cells.

The invention provides CAR(s) that comprise CTX or any functional variant thereof or a CTX-like peptide or any functional variant thereof as the extracellular antigen recognition moiety. CARs comprising CTX. CTX-like peptides or functional variants of the foregoing are collectively referred to herein as "CTX-CAR(s)". In certain embodiments, the CTX-CAR comprises a single CTX, CTX-like peptide or a functional variant of the foregoing. In certain embodiments, the CTX-CAR comprises more than one CTX polypeptide, CTX-like peptide or a functional variant of the foregoing, such as from 1 to 5 (for example, 1 to 2 or 2 to 3 or 2 to 4) CTX polypeptides, CTX-like peptides or a functional variants of the foregoing. When multiple CTX polypeptides and CTX-like peptides, including functional variants of the foregoing, are present, they may be positioned sequentially or non-sequentially in the extracellular domain and when positioned non-sequentially may optionally be separated by a peptide linker as described herein. Such CTX-CAR(s) may further comprise additional moieties or domains in the extracellular domain, a transmembrane domain and at least one intracellular signaling domain. CTX-CARs in accordance with the invention generally have the following structure: i) an extracellular domain (also referred to herein as an "ectodomain") comprising an antigen recognition domain/moiety comprising CTX or any functional variant thereof or a CTX-like peptide or any functional variant thereof, ii) a transmembrane domain and iii) an intracellular signaling domain (also referred to herein as an "endodomain"). In certain embodiments, a peptide linker from 1 to 30 amino acids may be present in the CTX-CAR to separate the various domains of the CAR. For example, a peptide linker may be present between the antigen recognition domain/moiety and other domains which may be present in the extracellular domain, between the antigen recognition domain/extracellular domain and the transmembrane domain or between the transmembrane domain and the intracellular signaling domain. A peptide linker may be present between all domains or only between a portion of the domains/moieties. Furthermore, when the intracellular signaling domain comprises more than one element, a linker peptide may be present between some or all of the individual elements in the endodomain.

The intracellular signaling domain of the CTX-CAR of the invention is responsible for activation of at least one of the normal effector functions of the host cell in which the CTX-CAR is placed. The term "effector function" refers to a specialized function of a differentiated cell. When the host cell is an immune effector cell, the intracellular signaling domain of the CTX-CAR of the invention is responsible for activation of at least one of a normal immune effector function. Immune effector function of a T cell, for example, may be cytolytic activity or helper activity, including, but not limited to, the secretion of cytokines. Immune effector function in a naive, stem-cell like, memory, or memory-type T cell includes, but is not limited to, antigen-dependent proliferation. Thus the term "intracellular signaling domain" refers to the portion of a CTX-CAR that transduces the effector function signal and directs the cell to perform a specialized function (for example, an effector function and/or an immune effector function). While usually the entire intracellular signaling domain will be employed, in many cases it will not be necessary to use the entire intracellular signaling domain. To the extent that a truncated portion of the intracellular signaling domain may find use, such truncated portion may be used in place of the intact signaling domain as long as such truncated portion still transduces the effector function/immune effector function signal. The term intracellular signaling domain is thus meant to include any truncated portion of the intracellular signaling domain sufficient to transduce the effector function/immune effector function signal. Examples of intracellular signaling domains include, but are not limited to, a signaling domain from the zeta chain of the T-cell receptor (CD3 zeta; CD247) or any of its homologs (e.g., eta, delta, gamma, or epsilon), MB1 chain, B29, FcRIII, FcRI, and combinations of signaling and/or costimulatory molecules, such as CD3 zeta chain and CD28, CD27, 4-1BB, DAP-10, OX40, and combinations thereof, as well as other similar molecules and fragments as well as mutations to the foregoing, such as modifying the immunoreceptor tyrosine-based activation motif(s) (ITAMs). In certain embodiments, the signaling domain comprises a CD3 zeta sequence, which may be represented by the sequence RVKFSRSADAPAYQQGQNQLY-NELNLGRREEYDVLDKRRGRDPEMGGKPRRKNP QEGLYNELQKDKMAEAYSEIGMKGERRRGKGHDG-LYQGLSTATKDTYDALHMQ ALPP R (SEQ ID NO: 26). Intracellular signaling portions of other members of the families of activating proteins can be used, such as FcγRIII and FcRI. One of skill in the art will be able to determine the corresponding signaling domains. Furthermore, any of the signaling domain sequences may contain from 1 to 5 amino acid modifications, which may be selected as discussed herein.

Preferably, the intracellular signaling domain of a CTX-CAR comprises a sequence encoding a costimulatory signaling domain. For example, the intracellular signaling domain can comprise a sequence encoding a primary signaling domain and a sequence encoding a costimulatory signaling domain. In certain embodiments, the costimulatory domain is a functional signaling domain from 41BB, OX40 and/or CD28. A costimulatory domain from OX40 may have the sequence ALYLLRRDQRLPP-DAHKPPGGGSFRTPIQEEQADAHSTLAKI (SEQ ID NO: 24). A costimulatory domain from CD28 may have the sequence RSKRSRLLHSDYMNMTPRRPGP-TRKHYQPYAPPRDFAAYRS (SEQ ID NO: 25). A costimulatory domain from 41BB may have the sequence KRGRKKLLY-IFKQPFMRPVQTTQEEDGCSCRFPEEEEGGCEL (SEQ ID NO: 27). Preferably, the encoded costimulatory signaling domain comprises a functional signaling domain of a protein chosen from one or more of CD27, CD28, 4-1BB (CD137). OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19. CD4, CD8a, CD8, IL2Rβ, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CDlla, LFA-1, ITGAM, CDlb, ITGAX, CDlc. ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229). CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, NKp44, NKp30, NKp46, or NKG2D. One of skill in the art will be able to determine the corresponding transmembrane regions from these polypeptides. Furthermore, any of the costimulatory domain sequences may contain from 1 to 5 amino acid modifications, which may be selected as discussed herein. In certain embodiments, the signaling domain comprises CD3 zeta-CD28-OX40, CD3 zeta-41BB, or CD2841BB and CD3 zeta-CD28-41BB.

Preferably the extracellular domain comprising the antigen recognition domain is linked to the intracellular signaling domain via an extracellular spacer and/or a transmembrane domain. The extracellular spacer preferably comprises all or a portion of an extracellular region of a transmembrane protein. Preferably, the extracellular spacer sequence comprises one or more of a hinge region and/or a portion of an immunoglobulin heavy chain constant region (which may comprise CH1, a linker region, CH2 and/or CH3 domains), or any combination thereof, of a human immunoglobulin, i.e. IgA, IgD, IgE, IgG, and IgM. In certain embodiments, extracellular spacer comprises all or a portion of the hinge region of human IgD. In certain embodiments, extracellular spacer comprises all or a portion of the hinge region of human IgG1. In certain embodiments, the extracellular spacer comprises all or a portion of the hinge region of human IgD and all or a portion of the hinge region of human IgG1. In certain embodiments, the extracellular spacer comprises all or a portion of the hinge region of human IgD and all or a portion of the CH2 and CH3 domains of the heavy chain constant region of human IgG1. In certain embodiments, the extracellular spacer comprises all or a portion of the hinge region of human IgD, all or a portion of the hinge region of human IgG1 and all or a portion of the CH2 and CH3 domains of the heavy chain constant region of human IgG1. In certain embodiments, extracellular spacer comprises all or a portion of the hinge region of human IgG1 and all or a portion of the CH2 and CH3 domains of the heavy chain constant region of human IgG1. In certain embodiments, extracellular spacer comprises all of the hinge region of human IgD, all or a portion of the hinge region of human IgG1 and the heavy chain constant region comprises all or a portion of the CH2 and CH3 domains of human IgG1. Preferably the hinge region amino acid sequence comprises the hinge region amino acid sequence from an immunoglobulin, such from IgD or IgG1, wherein the amino acid sequence comprises from 1 to 5 amino acid modifications, which may be selected as discussed herein. Preferably, the CH2 and CH3 domains of the heavy chain constant region comprises the CH2 and CH3 domain immunoglobulin heavy chain constant region amino acid sequence from an immunoglobulin, such from IgG1, wherein the amino acid sequence comprises from 1 to 5 amino acid modifications, which may be selected as discussed herein. In any of the foregoing, the extracellular spacer may further comprise a linker, such as a linker having the sequence of SEQ ID NO: 2 (Ser-Gly-Gly-Gly) or SEQ ID NO: 3 (Ser-Gly-Gly-Gly-Gly), which may be present having from 1 to 10 copies, linking the extracellular spacer to the extracellular domain comprising CTX or CTX-like peptide (or a functional variant of any of the foregoing).

In certain embodiments, the antigen recognition domain is linked to the transmembrane domain via a flexible linker. The flexible linker may be present in addition to the extracellular spacer or instead of the extracellular space described herein. In certain embodiments, the extracellular domain/antigen recognition domain is linked to the extracellular spacer via a flexible linker. Preferably the flexible linker comprises, for example, glycine and serine. Preferably, the flexible linker is comprised of a polypeptide having the sequence of SEQ ID NO: 2 (Ser-Gly-Gly-Gly)$_n$ or SEQ ID NO: 3 (Ser-Gly-Gly-Gly-Gly-Gly)$_n$, wherein n is an integer from 1 to 10. Preferably, each flexible linker is a polypeptide comprising from about 1-25 amino acids, preferably about 1-15 amino acids, preferably about 1-10 amino acids, preferably about 4-24 amino acids, preferably about 5-20 amino acids, preferably about 5-15 amino acids and preferably about 5-12 amino acids. Preferably, the linker is (Ser-Gly-Gly-Gly-Gly)$_n$ wherein n is 3.

Preferably, the CTX-CAR of the invention comprises a transmembrane domain that corresponds to, or is derived or obtained from, the transmembrane domain of any molecule known in the art. For example, the transmembrane domain can correspond to that of a CD8 molecule or a CD28 molecule. CD8 is a transmembrane glycoprotein that serves as a co-receptor for the T-cell receptor (TCR), and is expressed primarily on the surface of cytotoxic T-cells. The most common form of CD8 exists as a dimer composed of a CD8α and CD8β chain. CD28 is expressed on T-cells and provides co-stimulatory signals required for T-cell activation. A transmembrane domain from a CD8 polypeptide may have the sequence IYIWAPLAGT CGVLLLSLVI TLYC (SEQ ID NO: 23), particularly amino acids 1-21, 1-23 or 1-24 of SEQ ID NO: 23). CD28 is the receptor for CD80 (B7.1) and CD86 (B7.2). A transmembrane domain from a CD28 polypeptide may have the sequence FWVLVVVG GVLACYSLLV TVAFIIFWV (SEQ ID NO: 22). Preferably, the CD8 and CD28 are human. Preferred transmembrane domains of the CTX-CARs of the invention include, but are not limited to, all or a portion of a transmembrane domain from a polypeptide selected from: an alpha, beta or zeta chain of a T-cell receptor, CD28, CD3 epsilon, CD45, CD4, CD5. CD8. CD9, CD16, CD22, CD33, CD37, CD64, CD80, CD86, CD134, CD137, CD154, KIRDS2, OX40, CD2, CD27, LFA-1 (CDlla, CD18), ICOS (CD278), 4-1BB (CD137), GITR. CD40, BAFFR, HVEM (LIGHTR), SLAMF7, NKp80 (KLRF1), CD160, CD19, IL2Rβ, IL2R γ, IL7Rα, ITGA1, VLA1, CD49a, ITGA4, IA4, CD49D, ITGA6, VLA-6, CD49f, ITGAD, CDlld, ITGAE, CD103, ITGAL, CDl la, LFA-1, ITGAM, CDllb, ITGAX, CDl lc, ITGB1, CD29, ITGB2, CD18, LFA-1, ITGB7, TNFR2, DNAM1 (CD226), SLAMF4 (CD244, 2B4). CD84, CD96 (Tactile). CEACAM1, CRTAM, Ly9 (CD229), CD160 (BY55), PSGL1, CD100 (SEMA4D). SLAMF6 (NTB-A, Lyl08), SLAM (SLAMF1, CD150, IPO-3), BLAME (SLAMF8), SELPLG (CD162), LTBR, PAG/Cbp, NKp44, NKp30. NKp46, NKG2D, and/or NKG2C. One of skill in the art will be able to determine the corresponding transmembrane regions from these polypeptides.

The CTX-CAR can comprise any one of aforementioned transmembrane domains and any one or more (e.g., 1, 2, 3, or 4) of the aforementioned intracellular T-cell signaling domains in any combination. For example, a CTX-CAR can comprise a CD28 transmembrane domain and intracellular T-cell signaling domains of CD28 and CD3S. Furthermore, any of the transmembrane domain sequences may contain from 1 to 5 amino acid modifications, which may be selected as discussed herein.

Preferred CTX-CARs of the invention comprise an antigen recognition domain comprising CTX or a CTX-like peptide or functional variants of the foregoing, an optional linker linking the antigen recognition domain to the extracellular spacer; an extracellular spacer comprising all or a portion of a hinge region from an immunoglobulin molecule and and/or all or a portion of an immunoglobulin heavy chain constant region; a transmembrane region derived from the transmembrane region of an immune effector cell; and an intracellular signaling region comprising at least one signaling domain and an optional costimulatory signaling domain as described herein. The construct of a preferred CTX-CAR of the invention is shown in FIG. 1 (top panel) comprising an antigen recognition domain comprising CTX, a linker comprising (Ser-Gly-Gly-Gly)$_3$ (SEQ ID NO: 2); an extracellular spacer comprising a hinge region derived from the IgD hinge and the CH2CH3 domains of IgG1; a transmembrane region derived from the transmembrane region of CD-28; and an intracellular signaling region comprising CD28/Ox40 and CD3ζ. FIG. 1 (bottom panel) also shows a CTX construct lacking CTX or a CTX-like peptide or functional variants of the foregoing comprising a random peptide sequence (MRLNLIK) (SEQ ID NO: 5), a linker comprising (Ser-Gly-Gly-Gly)$_3$ (SEQ ID NO: 2); an extracellular spacer comprising a hinge region derived from the IgD hinge and the $CH_2CH_3$ domains of IgG1; a transmembrane region derived from the transmembrane region of CD-28; and an intracellular signaling region comprising CD28/Ox40 and CD3ζ. FIG. 2 shows the CTX-CAR and noCTX-CAR of FIG. 1 inserted into a membrane.

Other preferred CTX-CARs of the invention are shown in FIG. 3. The CTX-CAR of the construct at the top of FIG. 3 shows a typical first generation CTX-CAR comprising an antigen recognition domain comprising CTX, a linker comprising (Ser-Gly-Gly-Gly)$_3$ (SEQ ID NO: 2); an extracellular spacer comprising a hinge region derived from the IgD hinge and the CH2CH3 domains of IgG1; a transmembrane region derived from the transmembrane region of CD-28; and an intracellular signaling domain containing only CD3ζ. The construct at the bottom of FIG. 3 shows a CTX-CAR comprising an antigen recognition domain comprising CTX, a linker comprising (Ser-Gly-Gly-Gly)$_3$ (SEQ ID NO: 2); an extracellular spacer comprising a hinge region derived from the IgD hinge and the $CH_2CH_3$ domains of IgG1; a transmembrane region derived from the transmembrane region of CD-28; and lacking a functional intracellular signaling domain.

Included in the scope of the invention are functional portions of the CTX-CAR described herein. The term "functional portion," when used in reference to a CTX-CAR, refers to any part or fragment of the CAR of the invention, which part or fragment retains the biological activity of the CTX-CAR of which it is a part (the parent CTX-CAR). Functional portions encompass, for example, those parts of a CTX-CAR that retain the ability to recognize target cells, or detect, treat, or prevent a disease, to a similar extent, the same extent, or to a higher extent, as the parent CTX-CAR. In reference to a nucleic acid sequence encoding the parent CTX-CAR, a nucleic acid sequence encoding a functional portion of the CTX-CAR can encode a protein comprising, for example, about 10%, 25%, 30%, 50%, 68%, 80%, 90%, 95%, or more, of the parent CAR. A functional portion of a CTX-CAR can contain additional amino acids at the amino or carboxy terminus of the portion, or at both termini, which additional amino acids are not found in the amino acid sequence of the parent CTX-CAR. Desirably, the additional amino acids do not interfere with the biological function of the functional portion, e.g., recognize target cells, detect cancer, treat or prevent cancer, etc. More desirably, the additional amino acids enhance the biological activity of the CTX-CAR, as compared to the biological activity of the parent CTX-CAR.

The invention also provides functional variants of the inventive CTX-CAR. The term "functional variant," as used herein, refers to a CTX-CAR a polypeptide, or a protein having substantial or significant sequence identity or similarity to a CTX-CAR of the present disclosure, which functional variant retains the biological activity of the CTX- CAR of which it is a variant (the parent CTX-CAR). Functional variants encompass, for example, those variants of the parent CTX-CAR that retain the ability to recognize target cells to a similar extent, the same extent, or to a higher extent, as the parent CTX-CAR. In reference to a nucleic acid sequence encoding the parent CAR of the present disclosure, a nucleic acid sequence encoding a functional variant of the CTX-CAR can be for example, about 10% identical, about 25% identical, about 30% identical, about 50% identical, about 65% identical, about 80% identical, about 90% identical, about 95% identical, or about 99% identical to the nucleic acid sequence encoding the parent CTX-CAR.

A functional variant can, for example, comprise the amino acid sequence of the CTX-CAR with at least one amino acid modifications (such, as but not limited to, deletions, insertions and substitutions) can be selected, as would be known to one of ordinary skill in the art, to generate a desired CTX-CAR functional variant. Guidelines for selecting an amino acid modification are provided herein.

In one embodiment, the CTX-CAR of the present disclosure utilizes CTX as the extracellular antigen recognition moiety. In one embodiment, the CTX-CAR of the present disclosure utilizes CTX-like peptide as the extracellular antigen recognition moiety. In another embodiment, the CTX-CAR of the present disclosure utilizes a functional variant of CTX as the extracellular antigen recognition moiety. In another embodiment, the CTX-CAR of the present disclosure utilizes a functional variant of CTX as the extracellular antigen recognition moiety, wherein such functional variant of CTX contains one or more amino acid modifications (such, as but not limited to, deletions, insertions and substitutions) as compared to CTX (SEQ ID NO: 1). In another embodiment, the CTX-CAR of the present disclosure utilizes a functional variant of CTX as the extracellular antigen recognition moiety, wherein such functional variant of CTX comprises a sequence which has 70%, 80%, 90%, 95% or greater homology with SEQ ID NO: 1. In another embodiment, the CTX-CAR of the present disclosure utilizes a functional variant of a CTX-like peptide as the extracellular antigen recognition moiety. In another embodiment, the CTX-CAR of the present disclosure utilizes a functional variant of a CTX-like peptide as the extracellular antigen recognition moiety, wherein such functional variant of a CTX-like peptide contains one or more amino acid modifications (such, as but not limited to, deletions, insertions and substitutions) as compared to a CTX-like peptide of SEQ ID NOS: 6-21. In another embodiment, the CTX-CAR of the present disclosure utilizes a functional variant of a CTX-like peptide as the extracellular antigen recognition moiety, wherein such functional variant of a CTX-like peptide has 70%, 80%, 90%/o, 95% or greater homology with a sequence of SEQ ID NOS; 6-21.

In certain embodiments, a functional variant of CTX or a CTX-like peptide retains all of the cysteine residues (generally 6) present in the parent polypeptide (CTX or a CTX-like peptide). In certain embodiments, a functional variant has from 1-6 amino acid modifications (for example, a substitution, modification or deletion) with reference to the parent polypeptide (CTX or a CTX-like peptide). In certain embodiments, the functional variant has 1-2, 3-4 or 5-6 modifications. In certain embodiments, the amino acid modifications do not involve the cysteine residues (generally 6) present in the parent polypeptide (CTX or a CTX-like peptide).

The amino acid modifications (such, as but not limited to, deletions, insertions and substitutions) can be selected, as would be known to one of ordinary skill in the art, to generate a desired CTX and/or CTX-like peptide functional variant. For example, conservative substitutions or substitutions of amino acids with similar properties are expected to be tolerated. In addition, specific deletions, insertions and substitutions found in related polypeptides are expected to be well tolerated.

Conservative modifications to the amino acid sequence of SEQ ID NOS: 1 and 6-21 (and the corresponding modifications to the encoding nucleotides) will produce functional variants of CTX or a CTX-like peptide having functional and chemical characteristics similar to those of naturally occurring CTX or CTX-like peptide. The phrase "conservative amino acid substitution" or "conservative mutation" refers to the replacement of one amino acid by another amino acid with a common property. Examples of conservative mutations include amino acid substitutions of amino acids within the same amino acid subgroup, for example, lysine for arginine and vice versa such that a positive charge may be maintained; glutamic acid for aspartic acid and vice versa such that a negative charge may be maintained; serine for threonine such that a free —OH can be maintained; and glutamine for asparagine such that a free —NH$_2$ can be maintained. A "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine.

Conservative amino acid substitutions also encompass non-naturally occurring amino acid residues which are typically incorporated by chemical peptide synthesis rather than by synthesis in biological systems. These include peptidomimetics, and other reversed or inverted forms of amino acid moieties. It will be appreciated by those of skill in the art that nucleic acid and polypeptide molecules described herein may be chemically synthesized as well as produced by recombinant means.

Naturally occurring residues may be divided into classes based on common side chain properties: 1) hydrophobic: norleucine. Met, Ala, Val, Leu, lie; 2) neutral hydrophilic: Cys, Ser, Thr, Asn, Gln; 3) acidic: Asp, Glu; 4) basic: His, Lys, Arg; 5) residues that influence chain orientation: Gly, Pro; and 6) aromatic: Trp, Tyr, Phe.

Non-conservative amino acid substitutions are also contemplated, particularly when such non-conservative amino acids occur in related polypeptides with similar activity. For example, non-conservative substitutions may involve the exchange of a member of one of the amino acid classes for a member from another class. Such substituted residues may be introduced into regions of the CTX or CTX-like peptide functional variants that are homologous with related CTX polypeptide orthologs, or into the non-homologous regions of the molecule.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is understood in the art (Kyte et al., J. Mol. Biol., 157:105-131, 1982). It is known that certain amino acids may be substituted for other amino acids having a similar hydropathic index or score and still retain a similar biological activity. In making changes based upon the hydropathic index, the substitution of amino acids whose hydropathic indices are within +/−2 may be used; in an alternate embodiment, the hydropathic indices are with +/−1; in yet another alternate embodiment, the hydropathic indices are within +/−0.5.

It is also understood in the art that the substitution of like amino acids can be made effectively on the basis of hydrophilicity. The greatest local average hydrophilicity of a polypeptide as governed by the hydrophilicity of its adjacent amino acids, correlates with a biological property of the protein. The following hydrophilicity values have been assigned to amino acid residues: arginine (+3.0); lysine (+3.0); aspartate (+3.0.+−.1); glutamate (+3.0.+−.1); serine (+0.3); asparagine (+0.2); glutamine (+0.2); glycine (0); threonine (−0.4); proline (−0.5.+−.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within +/−2 may be used; in an alternate embodiment, the hydrophilicity values are with +/−1; in yet another alternate embodiment, the hydrophilicity values are within +/−0.5.

Desired amino acid substitutions (whether conservative or non-conservative) can be determined by those skilled in the art at the time such substitutions are desired. For example, amino acid substitutions can be used to identify important residues of a CTX or CTX-like polypeptide, or to increase or decrease the affinity of a CTX or CTX-like polypeptide with a particular binding target in order to increase or decrease an activity (for example, an effector function and/or an immune effector function) of a CTX-CAR of the present disclosure.

In one embodiment, a functional variant of CTX is one that shares 50%, 70%, 80%, 90%, 95% or more identify with respect to the amino acid sequence of SEQ ID NO: 1. In one embodiment, a functional variant of CTX is one that shares 80%, 90%, 95% or more identify with respect to the amino acid sequence of SEQ ID NO: 1. In one embodiment, a functional variant of CTX is one that shares 95% or more identify with respect to the amino acid sequence of SEQ ID NO: 1.

In one embodiment, a functional variant of a CTX-like polypeptide is one that shares 50%, 70%, 80%, 90%, 95% or more identify with respect to the amino acid sequence of one of SEQ ID NOS: 6-21. In one embodiment, a functional variant of a CTX-like polypeptide is one that shares 80%, 90%, 95% or more identify with respect to the amino acid sequence of one of SEQ ID NOS: 6-21. In one embodiment, a functional variant of a CTX-like polypeptide is one that shares 95% or more identify with respect to the amino acid sequence of one of SEQ ID NOS: 6-21.

In one embodiment, a functional variant of CTX is one that contains one or more substitutions at positions corresponding to positions 1, 3, 10, 13, 14, 17, 25 and 36 (positions with reference to SEQ ID NO: 1). In one aspect of such embodiment, preferable substitutions for such CTX functional variants at the indicated positions include: Arg for Met at position 1; Lys or Ser for Met at position 3; Pro or Gln for His at position 10; Ser or Thr for Ala at position 13; Lys for Arg at position 14; Ala or Tyr for Asp at position 17; Lys for Arg at position 25; and Ala for Arg at position 36. In certain aspects of such embodiments, the functional variant of CTX contains 6 or fewer substitutions from the indicated positions, 4 or fewer substitutions from the indicated positions or 2 or fewer substitutions from the indicated positions.

In one embodiment, a functional variant of CTX is one that contains one or more substitutions at positions corresponding to positions 9-11, 14-15, 17-18, 25 and 29, with or without a deletion of amino acids at positions 23 and 24 (positions with reference to SEQ ID NO: 1). In one aspect of such embodiment, preferable substitutions for such CTX functional variants at the indicated positions include: Arg for Asp at position 9; Pro or Gln for His at position 10; Asn or Asp for Gln at position 11; Lys, Gln or Asn for Arg at position 14; Arg or Gln for Lys at position 15; Asn, Ala, Arg or Tyr for Asp at position 17; Glu or Ala for Asp at position 18; Tyr, Lys, Ile, Gly or Asn for Arg at position 25; Phe for Tyr at position 29; and Asn or Ala for Arg at position 36. In another aspect of such embodiment, preferable substitutions for such CTX functional variants at the indicated positions include: Arg for Asp at position 9; Pro for His at position 10; Asn for Gln at position 11; Lys or Gln for Arg at position 14; Gln for Lys at position 15; Arg for Asp at position 17; Ala for Asp at position 18; Asn for Arg at position 25; Phe for Tyr at position 29; and Asn for Arg at position 36. In certain aspects of such embodiments, the functional variant of CTX contains 6 or fewer substitutions from the indicated positions, 4 or fewer substitutions from the indicated positions or 2 or fewer substitutions from the indicated positions.

In one embodiment, a functional variant of CTX is one that contains substitutions at positions corresponding to positions 1, 3, 9-15, 17-18, 21, 25-26, 29-31 and 36 with or without a deletion of amino acids at positions 23 and 24 (positions with reference to SEQ ID NO: 1). In one aspect of such embodiment, preferable substitutions for such CTX functional variants at the indicated positions include: Arg for Met at position 1; Lys, Ser or Gly for Met at position 3; Arg for Asp at position 9; Pro or Gln for His at position 10; Asn or Asp for Gln at position 11; Tyr for Met at position 12; Ser, Thr or Glu for Ala at position 13; Lys, Gln or Asn for Arg at position 14; Arg or Gln for Lys at position 15; Asn, Ala, Arg or Tyr for Asp at position 17; Glu or Ala for Asp at position 18; Arg or Lys for Gly at position 21; Tyr, Lys, Ile, Gly or Asn for Arg at position 25; Lys for Gly at position 27; Phe for Tyr at position 29; Phe for Gly at position 30; Gly or Tyr for Asp at position 31; and Asn or Ala for Arg at position 36. In certain aspects of such embodiments, the functional variant of CTX contains 12 or fewer substitutions from the indicated positions, 10 or fewer substitutions from the indicated positions, 8 or fewer substitutions from the indicated positions, 6 or fewer substitutions from the indicated positions, 4 or fewer substitutions from the indicated positions or 2 or fewer substitutions from the indicated positions.

In another embodiment, the functional variant of CTX is a polypeptide having the sequence of amino acids 2-36 of SEQ ID NO: 1. In one aspect of such embodiment, the CTX variant may have the amino acid substitutions described for amino acids 1, 3, 10, 13, 14, 17, 25 and 36, the amino acid substitutions described for amino acids 9-11, 14-15, 17-18, 25 and 29 above or the amino acid substitutions described for amino acids 1, 3, 9-15, 17-18, 21, 25-26, 29-31 and 36 above.

In another embodiment, the functional variant of CTX is a polypeptide having the sequence of amino acids 1-35 of SEQ ID NO: 1. In one aspect of such embodiment, the CTX variant may have the amino acid substitutions described for amino acids 1, 3, 10, 13, 14, 17, 25 and 36, the amino acid substitutions described for amino acids 9-11, 14-15, 17-18, 25 and 29 above or the amino acid substitutions described for amino acids 1, 3, 9-15, 17-18, 21, 25-26, 29-31 and 36 above.

In another embodiment, the functional variant of CTX is a polypeptide having the sequence of amino acids 2-35 of SEQ ID NO: 1. In one aspect of such embodiment, the CTX variant may have the amino acid substitutions described for amino acids 1, 3, 10, 13, 14, 17, 25 and 36, the amino acid substitutions described for amino acids 9-11, 14-15, 17-18, 25 and 29 above or the amino acid substitutions described for amino acids 1, 3, 9-15, 17-18, 21, 25-26, 29-31 and 36 above.

A CTX-CAR according to the present invention can be produced by any means known in the art, though preferably it is produced using recombinant DNA techniques. A nucleic acid sequence encoding the several regions of the CTX-CAR can prepared and assembled into a complete coding sequence by standard techniques of molecular cloning (genomic library screening, PCR, primer-assisted ligation, site-directed mutagenesis, etc.). The resulting coding region is preferably inserted into an expression vector and used to transform a suitable expression host cell line, such as an immune effector cells, preferably a T lymphocyte cell line, and most preferably an autologous T lymphocyte cell line, a third party derived T cell line/clone, a transformed humoral or xenogenic immunologic effector cell line, for expression of the CTX-CAR. Natural killer (NK) cells, macrophages, neutrophils, tumor-infiltrating-lymphocytes (TILs), lymphokine-activated killer (LAK) cells, memory T cells, regulatory T cells, cytotoxic T lymphocytes (CTLs), gamma delta T cells (γδ-T cells) and stem cells that differentiate into these cells, can also be used. Preferably γδ-T cells are used as the host cell line. As used herein, a "nucleic acid construct" or "nucleic acid sequence" is intended to mean a nucleic acid molecule, such as a DNA molecule, that can be transformed or introduced into an expression host cell line, such as, but not limited to, a T cell, and be expressed to produce a product (e.g., a chimeric receptor). Therefore, the invention further provides an isolated or purified nucleic acid sequence encoding the CTX-CARs of the invention. "Nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides. In the nucleic acid construct employed in the present invention, the promoter is operably linked to the nucleic acid sequence encoding a CTX-CAR of the present invention, i.e., they are positioned so as to promote transcription of the messenger RNA from the DNA encoding the chimeric receptor. The promoter can be of genomic origin or synthetically generated. A variety of promoters for use in T cells are well-known in the art. The promoter can be constitutive or inducible, where induction is associated with the specific cell type or a specific level of maturation, for example. Alternatively, a number of well-known viral promoters are also suitable. Promoters of interest include the β-actin promoter, SV40 early and late promoters, immunoglobulin promoter, human cytomegalovirus promoter, retrovirus promoter, and the Friend spleen focus-forming virus promoter. The promoters may or may not be associated with enhancers, wherein the enhancers may be naturally associated with the particular promoter or associated with a different promoter.

The various manipulations for preparing the CTX-CARs of the invention can be carried out in vitro and preferably the CTX-CAR chimeric construct is introduced into vectors for cloning and expression in an appropriate host cell using standard transformation or transfection methods. Thus, after each manipulation, the resulting construct from joining of the DNA sequences is cloned, the vector isolated, and the sequence screened to ensure that the sequence encodes the desired chimeric receptor. The sequence can be screened by restriction analysis, sequencing, or the like. Therefore, the invention comprises vectors encoding CTX-CARs of the invention or functional equivalents thereof.

Appropriate hosts cells for expressing the constructs of the invention include any immune effector cell which is capable of killing target cells when activated, preferably a T lymphocyte cell line, and most preferably an autologous T lymphocyte cell line, a third party derived T cell line/clone, a transformed humoral or xenogenic immunologic effector cell line. Natural killer (NK) cells, macrophages, neutrophils, tumor-infiltrating-lymphocytes (TILs), lymphokine-activated killer (LAK) cells, memory T cells, regulatory T cells, cytotoxic T lymphocytes (CTLs), gamma delta T cells (γδ-T cells) and stem cells that differentiate into these cells, can also be used. Preferably γδ-T cells are used as the host cell line.

As is well-known to one of skill in the art, various methods are readily available for isolating and expanding these cells from a subject. For example, using cell surface marker expression or using commercially available kits. It is contemplated that the chimeric construct can be introduced into the subject's own T cells as naked DNA or in a suitable vector. Methods of stably transfecting T cells by electroporation using naked DNA are known in the art. Naked DNA generally refers to the DNA encoding a chimeric receptor of the present invention contained in a plasmid expression vector in proper orientation for expression. Advantageously, the use of naked DNA reduces the time required to produce T cells expressing the chimeric receptor of the present invention.

Therefore, the invention comprises host cells containing (i.e., transformed or transduced with) vectors encoding CTX-CAR(s) of the invention, as well as functional variants thereof. Preferably the host cells are immune effector cells, preferably T-cells, a T lymphocyte cell line, and most preferably an autologous T lymphocyte cell line, a third party derived T cell line/clone, a transformed humoral or xenogenic immunologic effector cell line, for expression of the CTX-CAR. Natural killer (NK) cells, macrophages, neutrophils, tumor-infiltrating-lymphocytes (TILs), lymphokine-activated killer (LAK) cells, memory T cells, regulatory T cells, cytotoxic T lymphocytes (CTLs), gamma delta T cells (γδ-T cells) and stem cells that differentiate into these cells, can also be used. Preferably γδ-T cells are used as the host cell line. T-cells. Once it is established that the transfected or transduced T cell is capable of expressing the chimeric receptor as a surface membrane protein with the desired regulation and at a desired level, it can be determined whether the chimeric receptor is functional in the host cell to provide for the desired signal induction. Subsequently, the transduced T cells are reintroduced or administered to the subject to activate anti-tumor responses in the subject.

In one embodiment, the invention comprises host cells comprising (i.e., transformed or transduced with) at least one vector encoding (i.e., directing the expression of) a CTX-CAR(s) of the present disclosure, as well as functional variants thereof, and a survival factor as disclosed herein. Any CTX-CAR of the present disclosure may be used. Furthermore, the at least one vector may encode (i.e., directing the expression of) a stress-induced antigen receptor (such as but not limited to, NKG2D. As discussed herein, the survival factor allows the host cell to survive in a treatment environment created by an additional therapeutic treatment. In certain embodiments, a single vector encodes the CTX-CAR and the survival factor. In certain embodiments, a single vector encodes the CTX-CAR, the survival factor and the stress-induced antigen receptor. In certain embodiments, more than one vector encodes for the CTX-CAR, the survival factor and the stress-induced antigen receptor (for example, a vector encoding the CTX-CAR and the survival factor and a vector encoding the stress-induced antigen receptor).

In certain embodiments, the host cell comprising at least one vector directing the expression of a chimeric antigen receptor (CAR) and a survival factor (and optionally a stress-induced antigen receptor) is isolated or purified. In certain embodiments, the host cell comprising at least one vector directing the expression of a chimeric antigen receptor (CAR) and a survival factor (and optionally a stress-induced antigen receptor) is isolated or purified is a γδcell. Preferably the host cells expressing the CTX-CAR of the present disclosure are immune effector cells, preferably T-cells or NK cells, and more preferably γδT cells. Such host cells may be optionally engineered to express a survival factor (such as a polypeptide that confers resistance to one or more chemotherapy agents) that allows the host cell, for example, an immune effector cell, to survive in a treatment environment created by an additional therapeutic treatment (for example, a chemotherapeutic agent). Such cells are referred to herein as drug resistant (DR) cells and there use in therapy is referred to herein as "drug resistant immunotherapy" (DRI). DR cells and DRI is described in WO 2011/053750. the teachings of which are hereby incorporated by reference into the present application. The survival factor may be any factor known in the art that provides resistance to a treatment regimen and/or allows the cells comprising the survival factor and a CTX-CAR of the present disclosure to survive in a treatment environment (such as a chemotherapy treatment environment). In certain embodiments, the additional therapeutic treatment is treatment with a nucleoside-analog chemotherapy drug, alkylating agent, antimetabolite, antibiotic, topoisomerase inhibitor, mitotic inhibitor, differentiating agent, or hormone therapy agent and the survival factor provides resistance to the additional therapeutic treatment. In certain embodiments, the survival factor is MGMT, multidrug resistance protein 1 (MDR1), or 5' nucleotidase II (NT5C2). Other survival factors include, for example, a drug resistant variant of dihydrofolate reductase (L22Y-DHFR) and thymidylate synthase. Preferably, the survival factor in is MGMT. However, other survival factors may be used depending on the nature of the treatment environment (i.e., what other treatment regimens are being given to the patient in combination with the cells compositions of the present disclosure).

As used herein the phrase "survive in a treatment environment created by an additional therapeutic treatment" may be used interchangeably with the phrase, "survive in the presence of an additional therapeutic treatment" and each phrase refers to the ability of a host cell to survive direct contact with an agent used in the additional therapeutic treatment or to survive in the presence of cell toxicity in the environment of the cell compositions of the invention resulting from the use of an additional therapeutic treatment/agent while still performing its function. In one embodiment, the additional therapeutic treatment is treatment with an additional therapeutic agent. Additional therapeutic agents for use with DRI include, but are not limited to: alkylating agents (e.g., cyclophosphamide, ifosfamide, melphalan); metabolic antagonists (e.g., methotrexate (MTX), 5-fluorouracil or derivatives thereof); DNA demethylating agents (also known as antimetabolites; e.g., azacitidine); a substituted nucleotide; a substituted nucleoside; antitumor antibiotics (e.g., mitomycin, adriamycin); plant-derived antitumor agents (e.g., vincristine, vindesine, TAXOL®, paclitaxel, abraxane); cisplatin; carboplatin; etoposide; and the like. Such agents may further include, but are not limited to, the anti-cancer agents trimethotrexate (TMTX); temozolomide (TMZ); raltitrexed; S-(4-Nitrobenzyl)-6-thioinosine (NBMPR); 6-benzyguanidine (6-BG); nitrosoureas (for example, bis-chloroethylnitrosourea, also known as BCNU and carmustine, lomustine, also known as CCNU, +/−procarbazine and vincristine (PCV regimen) and fotemustine); doxorubicin; cytarabine; camptothecin; and a therapeutic derivative of any thereof.

DR immune effector cells, such as, but not limited to, T cells, NK cells and preferably γδT cells, expressing a CTX-CAR of the invention, may be produced by incorporating a nucleic acid construct coding for and capable of expressing a CTX-CAR described herein and a survival factor, and optionally other elements (for example, a suicide gene and/or a receptor for a stress-induced antigen). In certain embodiments, a single nucleic acid construct codes for the CTX-CAR and the survival factor, as well as the additional optional elements (for example, a suicide gene and/or a receptor for a stress-induced antigen). In certain embodiments, separate nucleic acid constructs code for each the CTX-CAR and the survival factor, and the optional other elements (for example, a suicide gene and/or a receptor for a stress-induced antigen). In certain embodiments, a single nucleic acid construct codes for the CTX-CAR and the survival factor and one or more nucleic acid constructs codes for the additional optional elements (for example, a suicide gene and/or a receptor for a stress-induced antigen).

Preferably the host cell expressing a CTX-CAR of the present disclosure (for example an immune effector cell, such as, but not limited to, T cells, NK cells and preferably γδ-T cells and including a DR immune effector cell) further comprises a receptor for a stress-induced antigen. In certain embodiments, the host cell expressing a CTX-CAR of the present disclosure further comprises a gene encoding for the stress-induced antigen receptor. In certain embodiments, the host cell expressing a CTX-CAR of the present disclosure naturally expresses the stress-induced antigen receptor. In certain embodiments, the DR immune effector cell further comprises a receptor for a stress-induced antigen. In certain embodiments, the DR immune effector cell expressing a CTX-CAR of the present disclosure naturally expresses the stress-induced antigen receptor. In certain embodiments of the foregoing, the stress-induced antigen receptor is an NKGD2. In certain embodiments, the stress-induced antigen receptor, including, but not limited to, the NKGD2 receptor is induced to an increased level on the host cell, including a DR immune effector cell.

Preferably the host cell expressing a CTX-CAR of the present disclosure (for example an immune effector cell, such as, but not limited to, T cells, NK cells and preferably γδ-T cells and including a DR immune effector cell) is a component of a composition that is administered to a subject.

In one embodiment, such composition comprises a host cell expressing a CTX-CAR of the present disclosure (for example an immune effector cell, such as, but not limited to, T cells, NK cells and preferably γδ-T cells and including a DR immune effector cell) and an additional immune system cell. For example, the composition may comprise γδ T cells expressing a CTX-CAR of the present disclosure and NK cells or may comprise γδ T cells expressing a CTX-CAR of the present disclosure and αβ T cells and NK cells. Preferably, the composition comprises γδ T cells expressing a CTX-CAR of the present disclosure and an additional immune system cell, wherein the γδ T cells are present at greater than or equal to 60% of the total cell population. In certain embodiments, the composition comprises γδ T cells expressing a CTX-CAR of the present disclosure and NK cells, wherein the γδ T cells are present at greater than or equal to 60% of the total cell population. In certain embodiments, the composition comprises γδ T cells expressing a CTX-CAR of the present disclosure and NK cells, wherein the γδ T cells are present at greater than or equal to 60% of the total cell population and the NK cells are present at less than or equal to 25%. In certain embodiments, the composition comprises γδ T cells expressing a CTX-CAR of the present disclosure and αc T cells, wherein the γδ T cells are present at greater than or equal to 60% of the total cell population. In certain embodiments, the composition comprises γδ T cells expressing a CTX-CAR of the present disclosure and αβ T cells, wherein the γδ T cells are present at greater than or equal to 60% of the total cell population and the αβ T cells are present at less than or equal to 5%. In certain embodiments, the composition comprises γδ T cells expressing a CTX-CAR of the present disclosure and αβ T cells and NK cells, wherein the γδ T cells are present at greater than or equal to 60% of the total cell population. In certain embodiments, the composition comprises γδ T cells expressing a CTX-CAR of the present disclosure and αβ T cells and NK cells, wherein the γδ T cells are present at greater than or equal to 60% of the total cell population, the αβ T cells are present at less than or equal to 5% of the total cell population and the NK cells are present at less than or equal to 25% of the total cell population.

Preferably, the composition comprising a host cell expressing a CTX-CAR of the present disclosure (for example an immune effector cell, such as, but not limited to, T cells, NK cells and preferably γδ-T cells and including a DR immune effector cell) comprises greater than or equal to 60%, 70%, 80%, 90%, 95% of a single type of immune system cell. In one aspect of the foregoing, the composition comprises greater than or equal to 60%, 70%, 80%, 90%, 95% of γδ T cells, wherein the γδ T cells express a CTX-CAR of the present disclosure. In one aspect of the foregoing the composition comprises greater than or equal to 60%, γδ T cells, wherein the γδ T cells express a CTX-CAR of the present disclosure, and less than or equal to 5% αβ T cells and less than or equal to 25% NK cells. The percentage of various cell types present, in one embodiment, is determined by flow cytometry.

The use of the survival factor (such as the MGMT gene), enables the compositions comprising a host cell expressing a CTX-CAR of the present disclosure (for example an immune effector cell, including a DR immune effector cell) of the present disclosure to survive in a treatment environment created by an additional therapeutic treatment at a time when the tumor is likely to be maximally stressed. The stress effect on the tumor in certain embodiments increases the expression of stress antigens, which are recognized by receptors, such as the NKG2D receptor, on the host cells (for example, γδ T cells). The dual effect of inducing stress antigens and decreasing regulatory T cells with chemotherapy significantly improve tumor reduction over either individual regimen. Gene modification protects the compositions of the present disclosure from the lymphodepleting effects of a chemotherapy regimen, for example TMZ, and allows the cell compositions of the present disclosure specific access to the tumor via TAA combined with unimpaired T cell cytotoxic function at the time that malignant cells are maximally stressed by chemotherapy. The use of DRI in combination with a CTX-CAR in accordance with the invention is referred to herein as "DRI CTX-CAR" therapy, is believed to significantly prolong survival and reduce tumor burden when compared with either chemotherapy (for example, TMZ) treatment alone or γδ T cell infusion, for example, alone and do so without significant adverse systemic or neurologic consequences.

To facilitate administration, the host cells expressing a CTX-CAR of the present disclosure (for example, immune effector cells such, but not limited to, as T cells, NK cells and preferably γδ-T cells) can be made into a composition, including a pharmaceutical composition, or made into an implant appropriate for administration in vivo, with appropriate carriers or diluents, which further can be pharmaceutically acceptable. The means of making such a composition or an implant have been described in the art. Where appropriate, the host cells expressing a CTX-CAR of the present disclosure can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Desirably, however, a pharmaceutically acceptable form is employed which does not ineffectuate the host cells expressing a CTX-CAR of the present disclosure. Thus, desirably the host cells expressing a CTX-CAR of the present disclosure can be made into a pharmaceutical composition containing a balanced salt solution, preferably Hanks' balanced salt solution, or normal saline. Therefore, the invention includes pharmaceutical compositions comprising host cells expressing a CTX-CAR of the present disclosure and host cells transformed or transduced with vectors of the invention. Suitably, the host cells are immune effector cells, for example, such as, but not limited to, T cells, NK cells and preferably γδ-T cells.

A pharmaceutical composition of the present invention can be used alone or in combination with other well-established agents useful for treating cancer. Whether delivered alone or in combination with other agents, the pharmaceutical composition of the present invention can be delivered via various routes and to various sites in a mammalian, particularly human, body to achieve a particular effect. One skilled in the art will recognize that, although more than one route can be used for administration, a particular route can provide a more immediate and more effective reaction than another route. For example, intradermal delivery may be advantageously used over inhalation for the treatment of melanoma. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration.

A composition of the present invention can be provided in unit dosage form wherein each dosage unit, e.g., an injection, contains a predetermined amount of the composition, alone or in appropriate combination with other active agents. The term unit dosage form as used herein refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically acceptable diluent, carrier, or vehicle, where appropriate. The specifications for the novel unit dosage forms of the present invention depend on the particular pharmacodynamics associated with the pharmaceutical composition in the particular subject.

Preferably, a therapeutically effective amount or sufficient number of the host cells expressing a CTX-CAR of the present disclosure, either present alone or as a part of a composition, is introduced into the subject such that a long-term, specific, response is established. In one embodiment, the response includes inhibition of cancer. In one embodiment, the response is the reduction in size of a tumor or elimination of tumor growth or regrowth or a reduction in metastasis to a greater degree than would otherwise result in the absence of such treatment with a CTX-CAR of the present disclosure. Desirably, the amount of host cells expressing a CTX-CAR of the present disclosure introduced into the subject causes a 10%, 20%, 30%, 40%, 50%, 60%, 70%, 80%, 90%, 95%, 98%, or 100% decrease in tumor size when compared to otherwise same conditions wherein the host cells expressing a CTX-CAR of the present disclosure are not present.

Accordingly, the amount of host cells expressing a CTX-CAR of the present disclosure administered should take into account the route of administration and should be such that a sufficient number of the host cells expressing a CTX-CAR of the present disclosure will be introduced so as to achieve the desired therapeutic response. Furthermore, the amounts of each host cells expressing a CTX-CAR of the present disclosure or other cell included in the compositions described herein (e.g., the amount per each cell to be contacted or the amount per certain body weight) can vary in different applications. In general, the concentration of host cells expressing a CTX-CAR of the present disclosure desirably should be sufficient to provide in the subject being treated at least from about $1\times10^5$ to about $1\times10^{10}$ host cells, even more desirably, from about $1\times10^7$ to about $5\times10^8$ host cells, although any suitable amount can be utilized either above, e.g., greater than $5\times10^8$ cells, or below, e.g., less than $1\times10^7$ cells. The dosing schedule can be based on well-established cell-based therapies or an alternate continuous infusion strategy can be employed.

These values provide general guidance of the range of host cells expressing a CTX-CAR of the present disclosure to be utilized by the practitioner upon optimizing the method of the present invention for practice of the invention. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on inter-individual differences in pharmacokinetics, drug disposition, and metabolism. One skilled in the art readily can make any necessary adjustments in accordance with the exigencies of the particular situation.

Suitable doses for a therapeutic effect would be between about $10^5$ and about $10^{10}$ host cells per dose, preferably in a series of dosing cycles. A preferred dosing regimen consists of four one-week dosing cycles of escalating doses, starting at about $10^5$ cells on Day 0, increasing incrementally up to a target dose of about $10^{10}$ cells by Day 5. Suitable modes of administration include intravenous, subcutaneous, intracavitary (for example by reservoir-access device), intraperitoneal, and direct injection into a tumor mass.

The invention also provides methods method of inhibiting growth of a cancer comprising contacting the cancer cell with a host cell expressing a CTX-CAR of the present disclosure. The invention also provides methods of treating cancer in a patient comprising administering to the patient a therapeutically effective amount of a host cell expressing a CTX-CAR of the present disclosure or a composition of the invention, such as a pharmaceutical composition, comprising such host cells. Preferably the cancer to be treated is of neuroectodermal origin. Preferably the cancer to be treated is a malignant glioma, melanoma, neuroblastoma, medulloblastoma or small cell lung carcinoma.

The invention includes cellular therapy where host cells (for example, immune effector cells such as T cells, NK cells and preferably γδ-T cells) are genetically modified to express a CTX-CAR and optionally genes for enabling DRI as described above, wherein such host cells are infused to a recipient in need thereof. The infused cells are able to kill tumor cells in the recipient. Unlike antibody therapies, host cells expressing a CTX-CAR are able to replicate in vivo resulting in long-term persistence that can lead to sustained tumor control.

The invention also includes a cellular therapy where host cells (for example, immune effector cells such as T cells. NK cells and preferably γδ-T cells) are modified to transiently express a CTX-CAR of the invention and optionally genes for enabling DRI, wherein such host cells are infused to a recipient in need thereof. The infused cells are able to kill tumor cells in the recipient. Thus, in various aspects, the immune effector cells (for example, immune effector cells such as, but not limited to, T cells, NK cells and preferably γδ-T cells) administered to the patient, is present for less than one month, e.g., three weeks, two weeks, one week, after administration of the immune effector cell to the patient.

In various aspects of such methods for cellular therapy, the host cells administered to the patient, or their progeny, persist in the patient for at least four months, five months, six months, seven months, eight months, nine months, ten months, eleven months, twelve months, thirteen months, fourteen months, fifteen months, sixteen months, seventeen months, eighteen months, nineteen months, twenty months, twenty-one months, twenty-two months, twenty-three months, two years, three years, four years, or five years after administration of the host cells to the patient.

In one aspect, the fully-human host cell expressing a CTX-CAR of the present disclosure (for example, immune effector cells, such as T cells. NK cells and preferably γδ-T cells) of the invention may be a type of vaccine for ex vivo immunization and/or in vivo therapy in a mammal. In one aspect, the mammal is a human. With respect to ex vivo immunization, at least one of the following occurs in vitro prior to administering the host cell or composition, including a pharmaceutical composition, comprising the host cell into a mammal: i) expansion of the host cells, ii) introducing a nucleic acid encoding a CTX-CAR to the host cells and/or iii) cryopreservation of the host cells expressing or capable of expressing the CTX-CAR. Fr vivo procedures are well known in the art. Briefly, cells are isolated from a patient (e.g., a human) and genetically modified so as to express a CTX-CAR of the present disclosure (i.e., transduced or transfected in vitro with a vector expressing a CTX-CAR disclosed herein). The CTX-CAR-modified host cell can be administered to a patient to provide a therapeutic benefit. The patient is preferably a human and the CTX-CAR-modified host cell can be autologous with respect to the patient. Alternatively, the host cells can be allogeneic, syngeneic or xenogeneic with respect to the patient.

A host cell expressing a CTX-CAR of the present disclosure herein may be used in combination with other known agents and therapies. In some embodiments, the delivery of one treatment is still occurring when the delivery of the second begins, so that there is overlap in terms of administration. This is sometimes referred to herein as "simultaneous" or "concurrent delivery". Preferably, the delivery of one treatment ends before the delivery of the other treatment begins. In either situation, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. Preferably, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A host cell expressing a CTX-CAR of the present disclosure, and the at least one additional therapeutic agent can be administered simultaneously, in the same or in separate compositions, or sequentially. For sequential administration, the host cell expressing a CTX-CAR of the present disclosure can be administered first, and the additional agent can be administered second, or the order of administration can be reversed.

The CTX-CAR therapy, DRI-CTX-CAR therapy and/or other therapeutic agents, procedures or modalities can be administered during periods of active disorder, or during a period of remission or less active disease. The CTX-CAR therapy or DRI-CTX-CAR therapy can be administered before the other treatment(s), concurrently with the other treatment (s), after the other treatment(s) (post-treatment), or during remission of the disorder.

When administered in combination, the CTX-CAR therapy or DRI-CTX-CAR therapy and the additional agent (e.g., second or third agent), the amount or dosage of one or all of the foregoing, can be administered in an amount or dose that is higher, lower or the same than the amount or dosage of each agent used individually. e.g., as a monotherapy. In certain embodiments of the CTX-CAR therapy, DRI-CTX-CAR therapy, the additional agent (e.g., second or third agent), the amount or dosage of one or all of the foregoing, is lower (e.g., at least 20%, at least 30%, at least 40%, or at least 50%) than the amount or dosage of each agent used individually, e.g., as a monotherapy. In other embodiments of the CTX-CAR therapy, DRI-CTX-CAR therapy, the additional agent (e.g., second or third agent), the amount or dosage of one or all of the foregoing, that results in a desired effect (e.g., inhibition of cancer) is lower (e.g., at least 20%6, at least 30%, at least 40%, or at least 50% lower) than the amount or dosage of each agent used individually, e.g., as a monotherapy, required to achieve the same therapeutic effect.

Preferably, host cell expressing a CTX-CAR of the present disclosure may be used in combination with an additional therapeutic treatment, such as, but not limited to, surgery, chemotherapy, check point inhibitors, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, FK506, rapamycin, mycophenolic acid, steroids, and cytokines. In certain embodiments, the host cell expressing a CTX-CAR of the present disclosure is further modified to be DR as described herein and used in DRI.

Any of the compositions described herein may be comprised in a kit. In a non-limiting example, a chimeric receptor expression construct, one or more reagents to generate a chimeric receptor expression construct, cells for transfection of the expression construct, and/or one or more instruments to obtain autologous cells for transfection of the expression construct (such an instrument may be a syringe, pipette, forceps, and/or any such medically approved apparatus). The kits may comprise one or more suitably aliquoted compositions of the present invention or reagents to generate compositions of the invention. The components of the kits may be packaged either in aqueous media or in lyophilized form. The container means of the kits may include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the chimeric receptor construct and any other reagent containers in close confinement for commercial sale. Such containers may include injection or blow molded plastic containers into which the desired vials are retained, for example.

EXAMPLES

The following examples are offered by way of illustration and are not to be construed as limiting the invention as claimed in any way.

Example 1-Methods for Generating a CTX-CAR and noCTX-CAR

To engineer T-cells expressing the CARs of the interest, CTX-CAR and the noCTX001-CAR genes were synthesized using G-block technology (IDT). Briefly, for the synthesis of the CTX-CAR the amino acid sequence of chlorotoxin (Scorpion venom; PRF: 445665) MCMPCFTTDHQ-MARKCDDCCGGKGRGKCYGPQCLCR (SEQ ID NO: 1) was converted to nucleotide using publicly available online software and codon optimized using the Integrated DNA technologies (IDT) online codon optimization tool having the sequence ATGTGTATGCCTTGCTTTACGACC-GATCATCAGATGGCTAGAAAGTGTGATGAC TGTTGTGGAGGCAAGGGACGAGGGAAATGC-TATGGACCTCAATGTTTGTGTCGC (SEQ ID NO: 4).

The optimized nucleotide sequence was synthesized using G-block technique (IDT), to be cloned in frame with CD8-alpha leader sequence at 5', and linker sequence SGGG ×3, an extracellular domain comprising the IgD hinge and IgG1 CH2 and CH3 domains, a transmembrane domain from CD28 and an intracellular signaling domain comprising CD28/Ox40/CD3S at 3'. The G-block was cloned using Infusion technique (Clontech) into the SFG vector encoding CD8alpha-IgD hinge, CH2CH3 (IgGH1) and TM domain, CD28/OX40/CD3ζ, and linearized using SphI and NotI restriction nucleases (NEB). The noCTX-CAR utilizes the same molecular scaffold, but includes an irrelevant peptide (SEQ ID NO: 5) instead of CTX (SEQ ID NO: 1) and was designed to be used as negative control in functional experiments. FIG. 1 shows the design of the CTX-CAR (top panel) and noCTX-CAR (bottom panel) constructs.

Both genes were then cloned into SphI and NotI sites of SFG retroviral vector using an In-Fusion kit (Clontech). Bacterial competent cells (Stellar. Clontech) were transformed with the ligation mix and plated on agar. Several bacterial clones were picked to prepare plasmid minipreps (Qiagen), which were tested to select correct plasmid constructs. The correct clones were selected based on the restriction pattern of the plasmid DNA cut with the restriction enzymes AfeI, XhoI, NcoI and NotI; the size of the DNA fragments was determined on agarose gel.

Example 2-Generating T Cells and Jurkat Cells Expressing the CTX-CAR and noCTX-CAR CTX-CAR and the noCTX-CAR vectors were used for transfection of 293T-cells together with gag-pol and env (RDF) plasmids to obtain viral supernatants. Resulting viruses were applied to transduce Jurkat E1-6 T-cell line in order to test expression of both CARs by flow cytometry using CH2CH3 AB (detecting the IgD Hinge of the CAR molecule). Subsequently, the transduction of T-cells with retroviral vectors encoding both CARs was performed.

Figure 4:
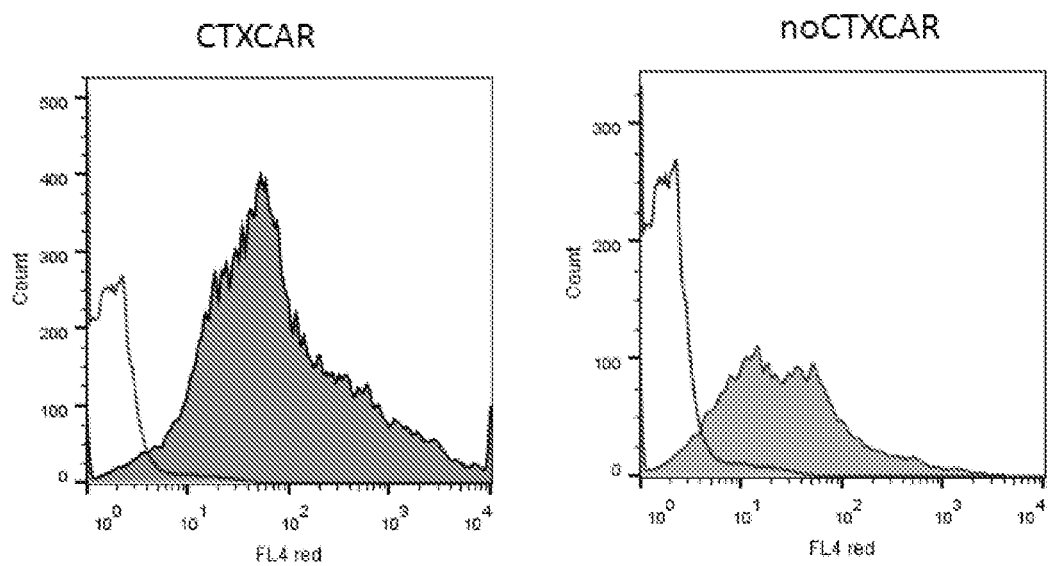
FIG. 4 are line graphs showing the transfection efficiency of 293T cells to obtain recombinant retroviruses comprising either a CTX-CAR described in Example 1 or a corresponding noCTX-CAR (each as illustrated in FIG. 1). The shaded graph shows 293T cells transfected with the CTX-CAR and noCTX-CAR and unshaded graph shows untransfected 293T cells. 293T cells were collected after 72 hours and stained with anti-CH2CH3 antibody (specific for CAR expression).

Briefly, 293T-cells were co-transfected with a) CTX-CAR or b) noCTX-CAR plasmids together with env (RDF114) and gag-pol (PEG-PAM) to obtain viral supernatants. 293T were collected after 72 hrs and stained with CH2CH3 antibody (to signify CAR expression). The unshaded portions in FIG. 4 show untransfected 293T-cells stained with CH2CH3 antibody and the shaded portion shows CTX-CAR transfected 293T-cells (left panel) and noCTX-CAR transfected 293T-cells (right panel). The results show that 293-T cells were efficiently transduced with both plasmid constructs.

Figures 5, 6:
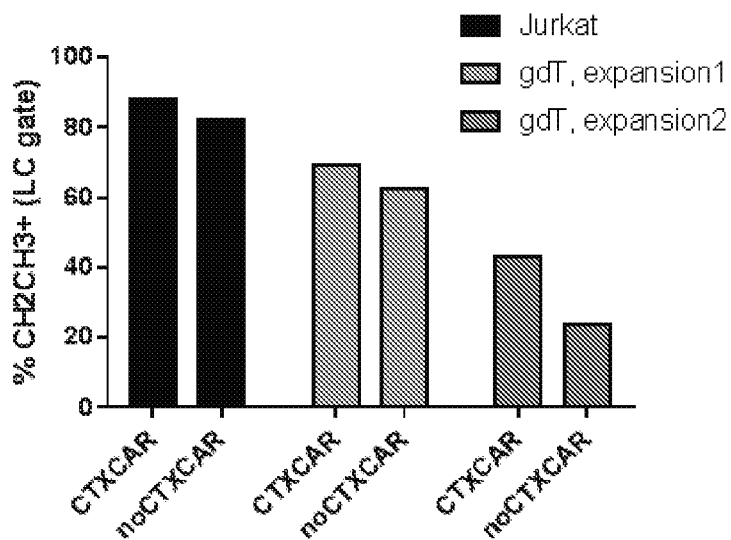
FIG. 5 is a bar graph showing transduction efficiency of Jurkat and gamma delta T-cells transduced with the CTX-CAR of Example 1 or the corresponding noCTX-CAR (each as illustrated in FIG. 1). Jurkat and γδ T cell expansion were transduced with CTX-CAR and noCTX-CAR viruses. Cells were collected after 72 hours and stained with $CH_2CH_3$ antibody.
FIG. 6 shows the various polypeptide and amino acid sequences disclosed herein.

Jurkat and γδT-cell expansions were transduced with CTX-CAR and noCTX-CAR viruses. Cells were collected after 72 hrs and stained with CH2CH3 antibody (to signify CAR expression). The Jurkat T-cells that were transduced with the viruses encoding CTX-CAR and noCTX-CAR expressed both transgenes on the cell surface, as shown in this experiment, where expression of the gene of interest was shown. Gamma delta T cells were efficiently transduced with resulting retroviruses and expression of both CARs was confirmed (FIG. 5).

Example 3—Jurkat Cells Expressing a CTX-CAR Selectively Bind Target Glioma Cells This example shows that effector cells expressing a CTX-CAR of the present disclosure selectively bind to glioma cells. Binding properties of effector cells expressing a CTX-CAR of the present disclosure or noCTX-CAR were tested using both glioma cells lines U87, U251 and LN229 as well as using primary human astrocytes (ScienCell Research Labs) (HA) and primary αβ T-cells (TLC). Jurkat cells were transduced with retroviruses encoding CTX-CAR or noCTX-CAR constructs shown in FIG. 1 and as described in Example 1 using the protocol described in Example 2.

Glioma cell lines and primary cell lines were grown under standard conditions. Adherent target cells were trypsinized and labeled with the green fluorescent dye calcein. Jurkat cells expressing a CTX-CAR of the present disclosure (CTX-CAR) or a noCTX-CAR (noCTX-CAR) were stained with an allophycocyanin (APC)-labelled anti-CH2CH3 antibody (which binds to the hinge region in the CTX-CAR and noCTX-CAR constructs). After staining, all labeled cells were washed, counted and mixed in a 1:1 ratio in 200 µl of PBS+1% BSA at 500,000 total cells/sample. Cell mixtures were incubated in solution under gentle agitation for 1 hr at RT. After gentle washing, samples of the cell mixtures were subjected to flow cytometry. The percentage of double-labeled cell population, corresponding to effector-target conglomerates, was determined by gating on the double stained FITC-APC population.

Figure 7:
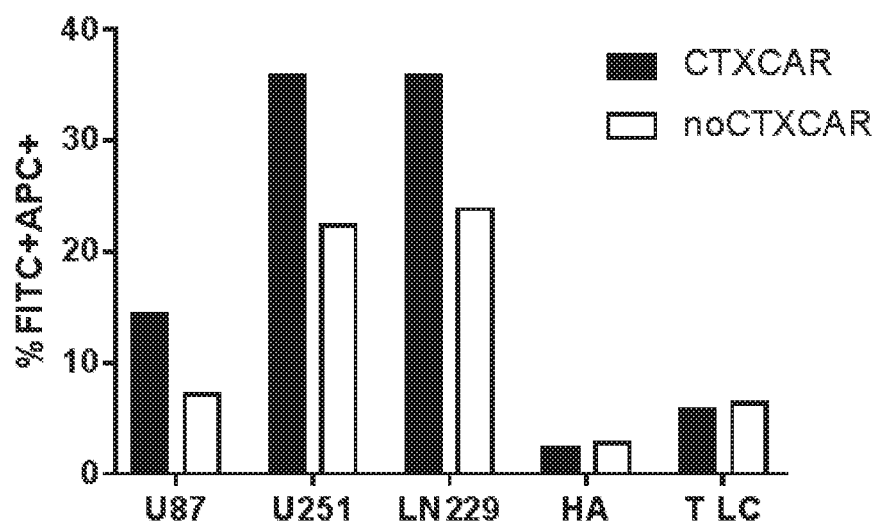
FIG. 7 shows Jurkat cells expressing a CTX-CAR of the present disclosure selectively bind to human glioma cell lines (U87; U251; and LN229) as compared to human primary cell lines (human astrocytes; HA; and αβ T-cells; T LC). Black bars indicate transduction with CTX-CAR and white bars indicate transduction with noCTX-CAR.

FIG. 7 shows that effector cells expressing a CTX-CAR of the present disclosure preferentially bound glioma cells lines with minimal binding to primary human astrocytes or primary human T-cells. The binding of effector cells expressing a CTX-CAR of the present disclosure showed increased binding to glioma cells as compared to effector cells expressing the noCTX-CAR construct. The binding of effectors cells expressing the CTX-CAR construct and the no-CTX-CAR construct was equivalent in primary human astrocytes and primary human T-cells.

The results demonstrate that the effector cells expressing a CTX-CAR of the present disclosure preferentially bind human glioma cells with minimal binding to the non-glioma cell lines tested.

Example 4—Cytotoxicity of T-Lymphocytes Expressing CTX-CAR

This example shows that effector cells expressing a CTX-CAR of the present disclosure are cytotoxic to glioma cells. Cytotoxicity was measured using the Bright-Glo Luciferase cytotoxicity assay kit (Promega). Target glioma cell lines U251 and U87 were infected with a lentivirus expressing a fusion protein of eGFP and firefly luciferase (GL) to allow the cells to be visualized by fluorescence and quantified by bioluminescent imaging (designated U251GL and U87GL).

PBMCs isolated from whole blood were activated using CD3/CD28 beads (for the activation and expansion of T-cells) for one day and transduced with retroviruses encoding CTX-CAR (CTX) or noCTX-CAR (noCTX) constructs shown in FIG. 1 and as described in Example 1. Efficiency of CAR expression was evaluated on day 4 after transduction and ranged from 40%-60%. Target glioma cells lines U251GL and U87GL were seeded to 96 well plates at 20,000 or 50,000 cell/well in 100 µl of complete media. CAR expressing T cells were added to wells in 100 ml of media at ratios target to effector (T:E) cell ratios of 1:2, 1:5, 1:10, 1:20 and incubated with target cells overnight at 37° C. As controls, target cell lines were incubated with mock transduced activated PBMC's (Mock) and Jurkat cells (Jurkat). After incubation, the 96 well plates were briefly spun and 150 µl of media was discarded. Bright-Glo kit reagent (serving to both lyse the cells and provide the luciferase substrate) was then added as per the manufacturer's instructions. After a 2 minute incubation, the cell lysates were transferred to the wells of flat bottom black 96 well plates and fluorescence was measured with an H1 Hybrid luminometer (Biotek).

Figure 8A:
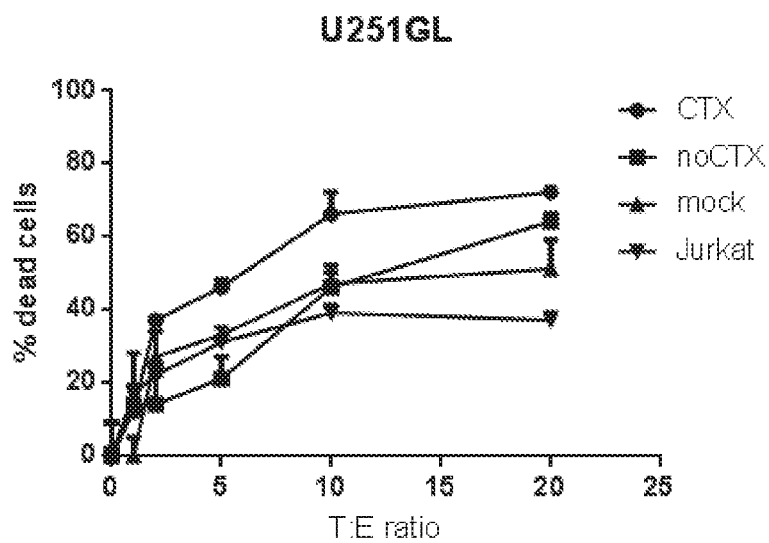
FIG. 8A shows the enhanced cytotoxicity of effector cells expressing a CTX-CAR of the present disclosure (CTX-CAR) against the glioma cell line U251GL as compared with effector cells expressing a CAR lacking CTX (noCTX-CAR), mock transduced effector cells (Mock) and Jurkat cells (Jurkat). Data is presented as % of specific luciferase reduction that correlates with number of dead cells in mixed culture.
Figure 8B:
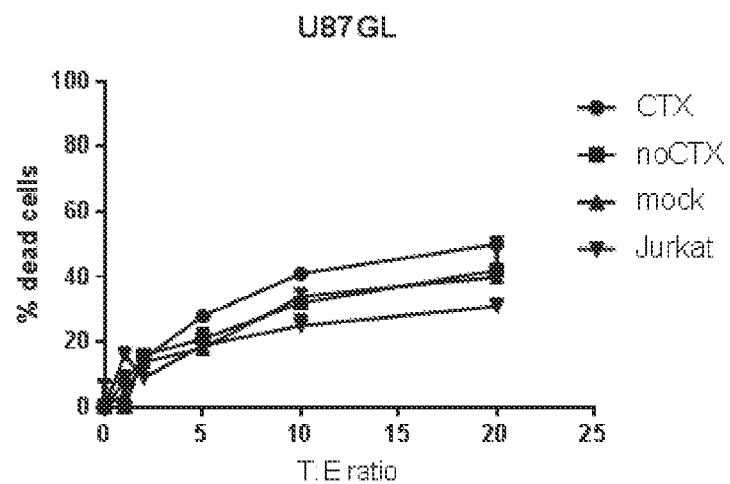
FIG. 8B shows the enhanced cytotoxicity of effector cells expressing a CTX-CAR of the present disclosure (CTX-CAR) against the glioma cell line U87GL as compared with effector cells expressing a CAR lacking CTX (noCTX-CAR), mock transduced effector cells (Mock) and Jurkat cells (Jurkat). Data is presented as % of specific luciferase reduction that correlates with number of dead cells in mixed culture.

FIG. 8A shows the effector cells transduced with a CTX-CAR of the present disclosure had enhanced cytotoxicity against U251GL glioma cells as compared to effector cells transduced with the same CAR construct lacking CTX. The enhanced cytotoxicity was enhanced at lower T:E ratios. Similar results are shown in FIG. 8B, illustrating the enhanced cytotoxicity of effector cells transduced with a CTX-CAR of the present disclosure against U87GL glioma cells.

The results demonstrate that the effector cells expressing a CTX-CAR of the present disclosure are cytotoxic to human glioma cells.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It will also be understood that none of the embodiments described herein are mutually exclusive and may be combined in various ways without departing from the scope of the invention encompassed by the appended claims.

---

What is claimed is:

1. A γδT cell comprising at least one vector, the at least one vector directing the expression of a chimeric antigen receptor (CAR) and a survival factor,
wherein the CAR comprises an extracellular domain comprising chlorotoxin, a transmembrane domain, and at least one intracellular signaling domain;
wherein the survival factor is a polypeptide that confers cellular resistance to a chemotherapeutic agent, and
wherein the γδT cell expresses an NKG2D receptor.

2. The γδT cell of claim 1, wherein the transmembrane domain is selected from the group consisting of: T-cell receptor alpha chain, T-cell receptor beta chain, T-cell receptor zeta chain, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1, ICOS, 4-1BB, GITR, CD40, BAFFR, HVEM, SLAMF7, NKp80, CD160, CD19, IL2RP, IL2Ry, IL7Ra, ITGA1, VLA1, CD49a, 1TGA4, IA4, CD49D, ITGA6, VLA-6, CD49f, ITGAD, CD11d, ITGAE, CD103, ITGAL, CD11a, ITGAM, CD11b, ITGAX, CD11c, ITGB1, CD29, ITGB2, CD18, ITGB7, TNFR2, DNAM1, SLAMF4, CD84, CD96, CEACAMI, CRTAM, Ly9, CD160, PSGL1, CD100, SLAMF6, SLAM, BLAME, SELPLG, LTBR, PAG/Cbp, NKp44, NKp30, NKp46, NKG2D, and NKG2C.

3. The γδT cell of claim 1, wherein the intracellular signaling domain is selected from the group consisting of: CD3 zeta, MB1 chain, B29, FcRIIL FcRI, and combinations of the foregoing.

4. The γδT cell of claim 3, wherein the intracellular signaling domain further comprises a costimulatory domain.

5. The γδT cell of claim 4, wherein the costimulatory domain comprises a functional signaling domain of a polypeptide selected from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD160, CD19, CD4, CD8a, CD80, IL2RP, IL2Ry, IL7Ra, ITGA4, VLA1, CD49a, ITGA4, IA4, CD49D, ITGA6, VLA-6, CD49f, ITGAD, CD11d, ITGAE, CD103, ITGAL, CD11a, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPG-3), BLAME (SLAMF8), SELPLG (CD162), LTBR, LAT, GADS, SLP-76, PAG/Cbp, NKp44, NKp30, NKp46, and NKG2D.

6. The γδT cell of claim 1, wherein the survival factor is selected from the group consisting of: $O^6$-methylguanine-DNA methyltransferase, multidrug resistance protein 1, 5' nucleotidase-II, dihydrofolate reductase and thymidilate synthase.

7. The γδT cell of claim 1, wherein the survival factor allows the γδT cell to survive in a treatment environment created by the chemotherapeutic agent.

8. The γδT cell of claim 7, wherein the chemotherapeutic agent is selected from the group consisting of: trimethotrexate, temozolomide, raltitrexed, S-(4-Nitrobenzyl)-6-thioinosine, 6-benzyguanidine, nitrosoureas, fotemustine, cytarabine, camptothecin, doxorubicin, melphalan, nitrosoureas, and any combination of the foregoing.

9. The γδT cell of claim 8, wherein the chemotherapeutic agent is temozolomide.

10. The γδT cell of claim 1, wherein the CAR further comprises an extracellular spacer.

11. The γδT cell of claim 10, wherein the extracellular spacer comprises all or a portion of a hinge region of human IgD or human IgGI and optionally all or a portion of an immunoglobulin heavy chain constant region from human IgGI.

12. The γδT cell of claim 1, wherein at least one vector directs the expression of a gene encoding the NKG2D receptor.

13. The γδT cell of claim 1, wherein the γδT cell naturally expresses a the NKG2D receptor.

14. The γδT cell of claim 1, wherein the γδT cell is isolated.

15. A pharmaceutical composition comprising γδT cells and a pharmaceutically acceptable carrier, wherein the γδT cells comprise at least one vector, the at least one vector directing the expression of a chimeric antigen receptor (CAR) and a survival factor,
wherein the CAR comprises an extracellular domain comprising chlorotoxin, a transmembrane domain, and at least one intracellular signaling domain;
wherein the survival factor is a polypeptide that confers cellular resistance to a chemotherapeutic agent, and
wherein the γδT cell expresses an NKG2D receptor.

16. The pharmaceutical composition of claim 15, wherein the γδT cells are present at greater than or equal to 60% of the total cell population of the composition as determined by flow cytometry.

17. The pharmaceutical composition of claim 15, wherein the survival factor is $O^6$-methylquanine-DNA methyltransferase.

* * * * *

SEQUENCE LISTING

<160> NUMBER OF SEQ ID NOS: 27

<210> SEQ ID NO 1
<211> LENGTH: 36
<212> TYPE: PRT
<213> ORGANISM: Leiurus quinquestriatus

<400> SEQUENCE: 1

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 2
<211> LENGTH: 4
<212> TYPE: PRT
<213> ORGANISM: Artificial Sequence
<220> FEATURE:
<223> OTHER INFORMATION: artificial linker

<400> SEQUENCE: 2

Ser Gly Gly Gly
1

<210> SEQ ID NO 3
<211> LENGTH: 5
<212> TYPE: PRT
<213> ORGANISM: Artificial Sequence
<220> FEATURE:
<223> OTHER INFORMATION: artificial linker

<400> SEQUENCE: 3

Ser Gly Gly Gly Gly
1               5

<210> SEQ ID NO 4
<211> LENGTH: 108
<212> TYPE: DNA
<213> ORGANISM: Artificial Sequence
<220> FEATURE:
<223> OTHER INFORMATION: optimized coding sequence

<400> SEQUENCE: 4
atgtgtatgc cttgctttac gaccgatcat cagatggcta gaaagtgtga tgactgttgt      60

```
ggaggcaagg gacgagggaa atgctatgga cctcaatgtt tgtgtcgc              108
```

<210> SEQ ID NO 5
<211> LENGTH: 7
<212> TYPE: PRT
<213> ORGANISM: Artificial Sequence
<220> FEATURE:
<223> OTHER INFORMATION: randomly generated peptide

<400> SEQUENCE: 5

Met Arg Leu Asn Leu Ile Lys
1               5

<210> SEQ ID NO 6
<211> LENGTH: 35
<212> TYPE: PRT
<213> ORGANISM: Buthus eupeus

<400> SEQUENCE: 6

Arg Cys Lys Pro Cys Phe Thr Thr Asp Pro Gln Met Ser Lys Lys Cys
1               5                   10                  15

Ala Asp Cys Cys Gly Gly Lys Gly Lys Gly Lys Cys Tyr Gly Pro Gln
            20                  25                  30

Cys Leu Cys
        35

<210> SEQ ID NO 7
<211> LENGTH: 35
<212> TYPE: PRT
<213> ORGANISM: Buthus eupeus

<400> SEQUENCE: 7

Met Cys Met Pro Cys Phe Thr Thr Asp His Asn Met Ala Lys Lys Cys
1               5                   10                  15

Arg Asp Cys Cys Gly Gly Asn Gly Lys Cys Phe Gly Pro Gln Cys Leu
            20                  25                  30

Cys Asn Arg
        35

<210> SEQ ID NO 8
<211> LENGTH: 38
<212> TYPE: PRT
<213> ORGANISM: Leiurus quinquestriatus

<400> SEQUENCE: 8

Arg Cys Ser Pro Cys Phe Thr Thr Asp Gln Gln Met Thr Lys Lys Cys
1               5                   10                  15

Tyr Asp Cys Cys Gly Gly Lys Gly Lys Gly Lys Cys Tyr Gly Pro Gln
            20                  25                  30

Cys Ile Cys Ala Pro Tyr
        35

<210> SEQ ID NO 9
<211> LENGTH: 36
<212> TYPE: PRT
<213> ORGANISM: Buthus eupeus

<400> SEQUENCE: 9

Met Cys Met Pro Cys Phe Thr Thr Asp His Gln Thr Ala Arg Arg Cys
1               5                   10                  15

Arg Asp Cys Cys Gly Gly Arg Gly Arg Lys Cys Phe Gly Gln Cys Leu
            20                  25                  30

```
Cys Gly Tyr Asp
        35

<210> SEQ ID NO 10
<211> LENGTH: 35
<212> TYPE: PRT
<213> ORGANISM: Buthus eupeus

<400> SEQUENCE: 10

Met Cys Met Pro Cys Phe Thr Thr Asp Pro Asn Met Ala Lys Lys Cys
1               5                   10                  15

Arg Asp Cys Cys Gly Gly Asn Gly Lys Cys Phe Gly Pro Gln Cys Leu
            20                  25                  30

Cys Asn Arg
        35

<210> SEQ ID NO 11
<211> LENGTH: 39
<212> TYPE: PRT
<213> ORGANISM: Buthus eupeus

<400> SEQUENCE: 11

Thr Glu Ala Met Cys Met Pro Cys Phe Thr Thr Asp His Asn Met Ala
1               5                   10                  15

Lys Lys Cys Arg Asp Cys Cys Gly Gly Asn Gly Lys Cys Phe Gly Tyr
            20                  25                  30

Gln Cys Leu Cys Asn Arg Gly
        35

<210> SEQ ID NO 12
<211> LENGTH: 34
<212> TYPE: PRT
<213> ORGANISM: Leiurus quinquestriatus

<400> SEQUENCE: 12

Cys Gly Pro Cys Phe Thr Thr Asp His Gln Met Glu Gln Lys Cys Ala
1               5                   10                  15

Glu Cys Cys Gly Gly Ile Gly Lys Cys Tyr Gly Pro Gln Cys Leu Cys
            20                  25                  30

Asn Arg

<210> SEQ ID NO 13
<211> LENGTH: 35
<212> TYPE: PRT
<213> ORGANISM: Buthus eupeus

<400> SEQUENCE: 13

Met Cys Met Pro Cys Phe Thr Thr Asp Pro Asn Met Ala Asn Lys Cys
1               5                   10                  15

Arg Asp Cys Cys Gly Gly Gly Lys Lys Cys Phe Gly Pro Gln Cys Leu
            20                  25                  30

Cys Asn Arg
        35

<210> SEQ ID NO 14
<211> LENGTH: 36
<212> TYPE: PRT
<213> ORGANISM: Buthus eupeus

<400> SEQUENCE: 14
```

```
Met Cys Met Pro Cys Phe Thr Thr Arg Pro Asp Met Ala Gln Gln Cys
1               5                   10                  15

Arg Ala Cys Cys Lys Gly Arg Gly Lys Cys Phe Gly Pro Gln Cys Leu
                20                  25                  30

Cys Gly Tyr Asp
            35

<210> SEQ ID NO 15
<211> LENGTH: 59
<212> TYPE: PRT
<213> ORGANISM: Buthus martensii

<400> SEQUENCE: 15

Met Lys Phe Leu Tyr Gly Ile Val Phe Ile Ala Leu Phe Leu Thr Val
1               5                   10                  15

Met Phe Ala Thr Gln Thr Asp Gly Cys Gly Pro Cys Phe Thr Thr Asp
                20                  25                  30

Ala Asn Met Ala Arg Lys Cys Arg Glu Cys Cys Gly Gly Asn Gly Lys
            35                  40                  45

Cys Phe Gly Pro Gln Cys Leu Cys Asn Arg Glu
    50                  55

<210> SEQ ID NO 16
<211> LENGTH: 50
<212> TYPE: PRT
<213> ORGANISM: Buthus martensii

<400> SEQUENCE: 16

Met Lys Phe Leu Tyr Gly Ile Val Phe Ile Ala Leu Phe Leu Thr Val
1               5                   10                  15

Met Phe Ala Thr Gln Thr Asp Gly Cys Gly Pro Cys Phe Thr Thr Asp
                20                  25                  30

Ala Asn Met Ala Arg Lys Cys Arg Glu Cys Cys Gly Gly Ile Gly Lys
            35                  40                  45

Cys Phe
    50

<210> SEQ ID NO 17
<211> LENGTH: 34
<212> TYPE: PRT
<213> ORGANISM: Androctonus australis

<400> SEQUENCE: 17

Met Cys Ile Pro Cys Phe Thr Thr Asn Pro Asn Met Ala Ala Lys Cys
1               5                   10                  15

Asn Ala Cys Cys Gly Ser Arg Arg Gly Ser Cys Arg Gly Pro Gln Cys
                20                  25                  30

Ile Cys

<210> SEQ ID NO 18
<211> LENGTH: 35
<212> TYPE: PRT
<213> ORGANISM: Buthus eupeus

<400> SEQUENCE: 18

Met Cys Met Pro Cys Phe Thr Thr Arg Pro Asp Met Ala Gln Gln Cys
1               5                   10                  15

Arg Asp Cys Cys Gly Gly Asn Gly Lys Cys Phe Gly Tyr Gln Cys Leu
                20                  25                  30
```

Cys Asn Arg
        35

<210> SEQ ID NO 19
<211> LENGTH: 36
<212> TYPE: PRT
<213> ORGANISM: Buthus sindicus

<400> SEQUENCE: 19

Cys Gly Pro Cys Phe Thr Lys Asp Pro Glu Thr Glu Lys Lys Cys Ala
1               5                   10                  15

Thr Cys Cys Gly Gly Ile Gly Arg Cys Phe Gly Pro Gln Cys Leu Cys
            20                  25                  30

Asn Arg Gly Tyr
        35

<210> SEQ ID NO 20
<211> LENGTH: 35
<212> TYPE: PRT
<213> ORGANISM: Androctonus mauretanicus

<400> SEQUENCE: 20

Cys Gly Pro Cys Phe Thr Thr Asp Pro Tyr Thr Glu Ser Lys Cys Ala
1               5                   10                  15

Thr Cys Cys Gly Gly Arg Gly Lys Cys Val Gly Pro Gln Cys Leu Cys
            20                  25                  30

Asn Arg Ile
        35

<210> SEQ ID NO 21
<211> LENGTH: 62
<212> TYPE: PRT
<213> ORGANISM: Buthus tamulus

<400> SEQUENCE: 21

Met Lys Phe Leu Tyr Gly Val Ile Leu Ile Ala Leu Phe Leu Thr Val
1               5                   10                  15

Met Thr Ala Thr Leu Ser Glu Ala Arg Cys Gly Pro Cys Phe Thr Thr
            20                  25                  30

Asp Pro Gln Thr Gln Ala Lys Cys Ser Glu Cys Cys Gly Arg Lys Gly
        35                  40                  45

Gly Val Cys Lys Gly Pro Gln Cys Ile Cys Gly Ile Gln Tyr
    50                  55                  60

<210> SEQ ID NO 22
<211> LENGTH: 27
<212> TYPE: PRT
<213> ORGANISM: Homo sapiens

<400> SEQUENCE: 22

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 23
<211> LENGTH: 24
<212> TYPE: PRT
<213> ORGANISM: Homo sapiens

<400> SEQUENCE: 23

```
Ile Tyr Ile Trp Ala Pro Leu Ala Gly Thr Cys Gly Val Leu Leu
1               5                   10                  15

Ser Leu Val Ile Thr Leu Tyr Cys
            20
```

<210> SEQ ID NO 24
<211> LENGTH: 42
<212> TYPE: PRT
<213> ORGANISM: Homo sapiens

<400> SEQUENCE: 24

```
Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
            35                  40
```

<210> SEQ ID NO 25
<211> LENGTH: 41
<212> TYPE: PRT
<213> ORGANISM: Homo sapiens

<400> SEQUENCE: 25

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40
```

<210> SEQ ID NO 26
<211> LENGTH: 112
<212> TYPE: PRT
<213> ORGANISM: Homo sapiens

<400> SEQUENCE: 26

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 27
<211> LENGTH: 42
<212> TYPE: PRT
<213> ORGANISM: Homo sapiens

<400> SEQUENCE: 27

```
Lys Arg Gly Arg Lys Lys Leu Leu Tyr Ile Phe Lys Gln Pro Phe Met
1               5                   10                  15
```

```
Arg Pro Val Gln Thr Thr Gln Glu Glu Asp Gly Cys Ser Cys Arg Phe
            20                  25                  30
Pro Glu Glu Glu Gly Gly Cys Glu Leu
        35              40
```